US012256937B2

(12) United States Patent
Zaidat et al.

(10) Patent No.: US 12,256,937 B2
(45) Date of Patent: Mar. 25, 2025

(54) SYSTEMS AND METHODS FOR TREATING ANEURYSMS

(71) Applicant: Galaxy Therapeutics, Inc., Milpitas, CA (US)

(72) Inventors: Osama O. Zaidat, Lambertville, MI (US); Aamir Badruddin, Bolingbrook, IL (US); Brett Follmer, Santa Clara, CA (US); Edgard Luiz Ramos Pereira, Boca Raton, FL (US); Arturo Rosqueta, San Jose, CA (US); Thomas J. Wolfe, Shorewood, WI (US)

(73) Assignee: Galaxy Therapeutics, Inc., Milpitas, CA (US)

( * ) Notice: Subject to any disclaimer, the term of this patent is extended or adjusted under 35 U.S.C. 154(b) by 0 days.

(21) Appl. No.: 18/629,658

(22) Filed: Apr. 8, 2024

(65) Prior Publication Data

US 2024/0374259 A1 Nov. 14, 2024

Related U.S. Application Data

(63) Continuation of application No. 18/298,069, filed on Apr. 10, 2023, now Pat. No. 11,969,171, which is a
(Continued)

(51) Int. Cl.
| | |
|---|---|
| *A61B 17/12* | (2006.01) |
| *A61B 17/00* | (2006.01) |
| *A61B 90/00* | (2016.01) |

(52) U.S. Cl.
CPC .. *A61B 17/12113* (2013.01); *A61B 17/00234* (2013.01); *A61B 17/12031* (2013.01);
(Continued)

(58) Field of Classification Search
CPC ........ A61B 17/00234; A61B 17/12031; A61B 17/12113; A61B 17/12122;
(Continued)

(56) References Cited

U.S. PATENT DOCUMENTS

| | | |
|---|---|---|
| 5,250,071 A | 10/1993 | Palermo |
| 5,282,806 A | 2/1994 | Haber et al. |

(Continued)

FOREIGN PATENT DOCUMENTS

| | | |
|---|---|---|
| CN | 102871700 B | 4/2015 |
| CN | 103006285 B | 6/2015 |

(Continued)

OTHER PUBLICATIONS

Shapiro, M., Raz, E., Becske, T., Nelson, P., "Variable Porosity of the Pipeline Embolization Device in Straight and Curved Vessels: A Guide for Optimal Deployment Strategy", Original Research Interventional, Sep. 26, 2013, 6 pages, 10.3174/ajnr.A3742, American Society of Neuroradiology, Oak Brook, USA.

(Continued)

*Primary Examiner* — Majid Jamialahmadi
(74) *Attorney, Agent, or Firm* — BLAIR WALKER IP SERVICES, LLC

(57) ABSTRACT

An apparatus for treating an aneurysm in a blood vessel includes an occlusion element including a first tubular mesh having a first end and a second end coupled together at a proximal end of the occlusion element such that an intermediate portion of the first tubular mesh between the first end and the second end includes a substantially 180 degree turn, the intermediate portion of the first tubular mesh extending distally from the proximal end of the occlusion element, wherein the intermediate portion of the first tubular mesh has a collapsed configuration and is configured to expand to an expanded. In some embodiments, the apparatus
(Continued)

further includes a second tubular mesh having a first end and a second end coupled to the proximal end of the occlusion element such that an intermediate portion of the second tubular mesh between the first end and the second end includes a substantially 180 degree turn. In some embodiments, the apparatus further comprises a cover coupled to the proximal end of the occlusion element.

20 Claims, 11 Drawing Sheets

Related U.S. Application Data continuation of application No. 17/516,976, filed on Nov. 2, 2021, now Pat. No. 11,622,771, which is a continuation of application No. 16/840,415, filed on Apr. 5, 2020, now Pat. No. 11,202,636.

(60) Provisional application No. 62/975,744, filed on Feb. 12, 2020, provisional application No. 62/975,741, filed on Feb. 12, 2020, provisional application No. 62/914,442, filed on Oct. 12, 2019, provisional application No. 62/852,988, filed on May 25, 2019.

(52) U.S. Cl.
CPC .. *A61B 17/12172* (2013.01); *A61B 17/12177* (2013.01); *A61B 2017/00867* (2013.01); *A61B 2017/1205* (2013.01); *A61B 2017/12054* (2013.01); *A61B 2017/12059* (2013.01); *A61B 2017/12063* (2013.01); *A61B 2017/12068* (2013.01); *A61B 2090/3966* (2016.02)

(58) Field of Classification Search
CPC ........ A61B 17/12172; A61B 17/12027; A61B 17/12036; A61B 17/1204; A61B 2017/00867; A61B 2017/1205; A61B 2017/12054

See application file for complete search history.

(56) References Cited

U.S. PATENT DOCUMENTS

| | | | |
|---|---|---|---|
| 5,304,195 A | 4/1994 | Twyford, Jr. et al. |
| 5,556,390 A | 9/1996 | Hicks |
| 5,795,331 A | 8/1998 | Cragg et al. |
| 5,935,148 A | 8/1999 | Villar et al. |
| 6,086,577 A | 7/2000 | Ken et al. |
| 6,152,144 A | 11/2000 | Lesh et al. |
| 6,391,037 B1 | 5/2002 | Greenhalgh |
| 6,454,780 B1 | 9/2002 | Wallace |
| 6,506,204 B2 | 1/2003 | Mazzochi |
| 6,544,163 B2 | 4/2003 | Wallace et al. |
| 6,613,074 B1 | 9/2003 | Mitelberg et al. |
| 6,936,055 B1 | 8/2005 | Ken et al. |
| 6,994,689 B1 | 2/2006 | Zadno-Azizi et al. |
| 7,128,736 B1 | 10/2006 | Abrams et al. |
| 7,195,636 B2 | 3/2007 | Avellanet et al. |
| 7,229,461 B2 | 6/2007 | Chin et al. |
| 7,410,482 B2 | 8/2008 | Murphy et al. |
| 7,569,066 B2 | 8/2009 | Gerberding et al. |
| 7,749,242 B2 | 7/2010 | Tran et al. |
| 8,142,456 B2 | 3/2012 | Rosqueta et al. |
| 8,333,796 B2 | 12/2012 | Tompkins et al. |
| 8,388,650 B2 | 3/2013 | Gerberding et al. |
| 8,398,670 B2 | 3/2013 | Amplatz et al. |
| 8,551,132 B2 | 10/2013 | Eskridge et al. |
| 8,597,320 B2 | 12/2013 | Sepetka et al. |
| 8,728,117 B1 | 5/2014 | Janardhan et al. |
| 8,777,979 B2 | 7/2014 | Shrivastava et al. |
| 8,820,207 B2 | 9/2014 | Marchand et al. |
| 8,826,791 B2 | 9/2014 | Thompson et al. |
| 8,864,790 B2 | 10/2014 | Strauss et al. |
| 8,864,791 B2 | 10/2014 | Bloom et al. |
| 8,940,015 B2 | 1/2015 | Kariniemi |
| 8,998,947 B2 | 4/2015 | Aboytes et al. |
| 9,107,670 B2 | 8/2015 | Hannes et al. |
| 9,198,668 B2 | 12/2015 | Theobald et al. |
| 9,259,337 B2 | 2/2016 | Cox et al. |
| 9,314,326 B2 | 4/2016 | Wallace et al. |
| 9,510,811 B2 | 12/2016 | Akpinar |
| 9,585,670 B2 | 3/2017 | Hines |
| 9,597,087 B2 | 3/2017 | Marchand et al. |
| 9,636,117 B2 | 5/2017 | Bachman et al. |
| 9,669,188 B2 | 6/2017 | Echarri et al. |
| 9,855,052 B2 | 1/2018 | Aboytes et al. |
| 9,918,720 B2 | 3/2018 | Marchand et al. |
| 9,980,733 B2 | 5/2018 | Badruddin et al. |
| 10,111,670 B2 | 10/2018 | Lorenzo et al. |
| 10,136,896 B2 | 11/2018 | Hewitt et al. |
| 10,149,676 B2 | 12/2018 | Mirigian et al. |
| 10,478,195 B2 | 11/2019 | Aboytes et al. |
| 2002/0169473 A1 | 11/2002 | Sepetka et al. |
| 2002/0188314 A1 | 12/2002 | Anderson et al. |
| 2003/0171770 A1 | 9/2003 | Kusleika et al. |
| 2003/0176884 A1 | 9/2003 | Berrada et al. |
| 2003/0195553 A1 | 10/2003 | Wallace et al. |
| 2004/0034386 A1 | 2/2004 | Fulton et al. |
| 2004/0044391 A1 | 3/2004 | Porter |
| 2004/0111112 A1 | 6/2004 | Hoffmann |
| 2004/0172056 A1* | 9/2004 | Guterman ........ A61B 17/12186 623/1.11 |
| 2004/0199201 A1 | 10/2004 | Kellett et al. |
| 2005/0033409 A1 | 2/2005 | Burke et al. |
| 2005/0107823 A1 | 5/2005 | Leone et al. |
| 2005/0171478 A1 | 8/2005 | Selmon et al. |
| 2005/0277978 A1 | 12/2005 | Greenhalgh |
| 2006/0064151 A1* | 3/2006 | Guterman ................. A61F 2/07 623/1.3 |
| 2006/0106417 A1 | 5/2006 | Tessmer et al. |
| 2006/0155323 A1 | 7/2006 | Porter et al. |
| 2007/0083257 A1 | 4/2007 | Pal et al. |
| 2007/0173928 A1 | 7/2007 | Morsi |
| 2007/0208376 A1 | 9/2007 | Meng |
| 2007/0225794 A1 | 9/2007 | Thramann et al. |
| 2007/0270902 A1 | 11/2007 | Slazas et al. |
| 2008/0045997 A1 | 2/2008 | Balgobin et al. |
| 2008/0097495 A1 | 4/2008 | Feller, III et al. |
| 2008/0147100 A1 | 6/2008 | Wallace |
| 2008/0281350 A1 | 11/2008 | Sepetka et al. |
| 2008/0319533 A1 | 12/2008 | Lehe |
| 2009/0062841 A1 | 3/2009 | Amplatz et al. |
| 2009/0082803 A1 | 3/2009 | Adams et al. |
| 2009/0099647 A1 | 4/2009 | Glimsdale et al. |
| 2009/0177261 A1 | 7/2009 | Teoh et al. |
| 2009/0264978 A1 | 10/2009 | Dieck et al. |
| 2009/0287291 A1 | 11/2009 | Becking et al. |
| 2009/0318941 A1 | 12/2009 | Sepetka et al. |
| 2010/0106240 A1 | 4/2010 | Duggal et al. |
| 2010/0179583 A1 | 7/2010 | Carpenter et al. |
| 2011/0046719 A1 | 2/2011 | Frid |
| 2011/0202085 A1 | 8/2011 | Loganathan et al. |
| 2012/0065667 A1 | 3/2012 | Javois et al. |
| 2012/0071911 A1 | 3/2012 | Sadasivan et al. |
| 2012/0143317 A1 | 6/2012 | Cam et al. |
| 2012/0259244 A1 | 10/2012 | Roberts et al. |
| 2012/0283768 A1 | 11/2012 | Cox et al. |
| 2012/0303052 A1 | 11/2012 | Connor |
| 2012/0310270 A1 | 12/2012 | Murphy et al. |
| 2012/0330347 A1 | 12/2012 | Becking et al. |
| 2013/0066357 A1 | 3/2013 | Abotes et al. |
| 2013/0073026 A1 | 3/2013 | Russo et al. |
| 2013/0190800 A1 | 7/2013 | Murphy et al. |
| 2013/0211495 A1 | 8/2013 | Halden et al. |
| 2014/0005714 A1 | 1/2014 | Quick et al. |
| 2014/0012303 A1 | 1/2014 | Heipl |
| 2014/0052233 A1 | 2/2014 | Cox et al. |
| 2014/0172001 A1 | 6/2014 | Becking et al. |
| 2014/0257360 A1 | 9/2014 | Keillor |
| 2014/0343602 A1 | 11/2014 | Cox et al. |
| 2015/0005811 A1 | 1/2015 | Lubock et al. |

(56) References Cited

U.S. PATENT DOCUMENTS

| | | |
|---|---|---|
| 2015/0133989 A1 | 5/2015 | Lubock et al. |
| 2015/0250628 A1 | 9/2015 | Monstadt et al. |
| 2015/0272589 A1 | 10/2015 | Lorenzo |
| 2015/0313605 A1 | 11/2015 | Griffin |
| 2016/0022445 A1 | 1/2016 | Ruvalcava et al. |
| 2016/0030050 A1 | 2/2016 | Franano et al. |
| 2016/0278749 A1 | 9/2016 | Javois et al. |
| 2016/0317277 A1 | 11/2016 | Carpenter et al. |
| 2017/0014114 A1 | 1/2017 | Radfiee et al. |
| 2017/0156734 A1 | 6/2017 | Griffin |
| 2017/0224350 A1 | 8/2017 | Shimizu et al. |
| 2017/0224355 A1 | 8/2017 | Bowman et al. |
| 2017/0348014 A1 | 12/2017 | Wallace et al. |
| 2017/0367708 A1 | 12/2017 | Mayer et al. |
| 2017/0367713 A1 | 12/2017 | Greene, Jr. et al. |
| 2018/0049731 A1 | 2/2018 | Hardy et al. |
| 2019/0053810 A1 | 2/2019 | Griffin |
| 2019/0110796 A1 | 4/2019 | Jayaraman |
| 2019/0192165 A1 | 6/2019 | Greene, Jr. et al. |
| 2019/0192167 A1* | 6/2019 | Lorenzo ............ A61B 17/12031 |
| 2019/0192168 A1 | 6/2019 | Lorenzo |
| 2019/0223876 A1 | 7/2019 | Badruddin et al. |
| 2019/0223881 A1 | 7/2019 | Hewitt et al. |
| 2019/0357914 A1 | 11/2019 | Gorochow et al. |
| 2020/0113576 A1 | 4/2020 | Gorochow et al. |
| 2020/0305885 A1 | 10/2020 | Soto Del Valle et al. |

FOREIGN PATENT DOCUMENTS

| | | |
|---|---|---|
| DE | 102012016555 A1 | 2/2014 |
| DE | 102013006503 A1 | 7/2014 |
| EP | 0832607 A1 | 4/1998 |
| EP | 3146916 A1 | 3/2017 |
| EP | 2647343 B1 | 7/2017 |
| WO | WO1999/05977 A1 | 2/1999 |
| WO | WO2002/00139 A1 | 1/2002 |
| WO | WO2009132045 A2 | 10/2009 |
| WO | WO2012009675 A2 | 1/2012 |
| WO | WO2013138615 A2 | 9/2013 |
| WO | WO2013184595 A1 | 12/2013 |
| WO | WO2015057796 A1 | 4/2015 |
| WO | WO2015168249 A1 | 11/2015 |
| WO | WO2017/102804 A1 | 6/2017 |
| WO | WO2017/153603 A1 | 9/2017 |
| WO | WO2017/220400 A1 | 12/2017 |
| WO | WO2019038293 A1 | 2/2019 |

OTHER PUBLICATIONS

Perez, M., Henkes, H., Bouillot, P., Brina, O., Slater, L., Pereira, V., "Intra-aneurysmal hemodynamics: evaluation of pCONus and pCANvas bifurcation aneurysm devices using DSA optical flow imaging", Journal of NeuroInterventional Surgery, Dec. 23, 2015, 6 pages, 10.1136/neurintsurg-2015-011927, Society of NeuroInterventional Surgery, Fairfax, USA.

Torii, R., Oshima, M., Kobayashi, T., Takagi, K., Tezduyar, T., "Fluid-structure interaction modeling of a patient-specific cerebral aneurysm: influence of structural modeling." Computational Mechanics 43: 151-159 (2008).

Control, etc. http://www.asianjns.org/articles/2012/7/4/images/AsianJNeurosurg_2012_7_4_159_106643_f7.jpg downloaded from internet Apr. 3, 2020.

Cerus https://neuronewsinternational-wpengine.netdna-ssl.com/wp-content/uploads/sites/Mar. 2016/07/Cerus-Endovascular-Contour-300x194.jpg downloaded from internet Apr. 3, 2020.

Contour https://neuronewsinternational-wpengine.netdna-ssl.com/wp-content/uploads/sites/Mar. 2017/06/Contour- e1497957260381-300x194.png downloaded from internet 2020-04-03.

Medtronic https://evtoday.com/images/articles/2017-02/0217-endovascular-fig1.png downloaded from internet Apr. 3, 2020.

Bhogal, P., Udani, S., Cognard, C., Piotin, M., Brouwer, P., Sourour, N., Andersson, T., Makalanda, L., Wong, K., Fiorella, D., Arthur, A., Yeo, L., Soderman, M., Henkes, H., Pierot, L., "Endovascular flow disruption: where are we now?" Journal of Neurointerventional Surgery 11: 1024-1035 (2019).

PCT International Search Report and Written Opinion for PCT/US2020/034450, Galaxy Therapeutics, Inc., Forms PCT/ISA/220, 210, and 237 dated Aug. 1, 2020 (11 pages).

Extended European Search Report dated Nov. 11, 2022, in EP App. No. 20815001.1 filed May 25, 2020 (8 pages).

\* cited by examiner

SYSTEMS AND METHODS FOR TREATING ANEURYSMS

INCORPORATION BY REFERENCE TO ANY PRIORITY APPLICATIONS

This application is a continuation of U.S. patent application Ser. No. 18/298,069, filed on Apr. 10, 2023, now U.S. Pat. No. 11,969,171, which is a continuation of U.S. patent application Ser. No. 17/516,976, filed on Nov. 2, 2021, now U.S. Pat. No. 11,622,771, which is a continuation of U.S. patent application Ser. No. 16/840,415, filed on Apr. 5, 2020, now U.S. Pat. No. 11,202,636, which claims the benefit of priority to U.S. Provisional Patent Application No. 62/852,988, filed on May 25, 2019, U.S. Provisional Patent Application No. 62/914,442, filed on Oct. 12, 2019, U.S. Provisional Patent Application No. 62/975,741, filed on Feb. 12, 2020, and U.S. Provisional Patent Application No. 62/975,744, filed on Feb. 12, 2020, all of which are herein incorporated by reference in their entirety for all purposes. Priority is claimed pursuant to 35 U.S.C. § 120 and 35 U.S.C. § 119.

BACKGROUND OF THE INVENTION

Field of the Invention

The field of the invention generally relates to embolic devices for filling spaces in the vascular system, including cerebral aneurysms or left atrial appendages. In some case, the embolic devices may be used to embolize native vessels.

Description of the Related Art

An embolic device may be used as a stand-alone device to occlude and aneurysm, or may be used with an adjunctive device or material.

SUMMARY OF THE INVENTION

In one embodiment of the present disclosure, an apparatus for treating an aneurysm in a blood vessel includes an occlusion element configured to be releasably coupled to an elongate delivery shaft, the occlusion element including a cover having a mesh material and configured to be delivered in a collapsed configuration through an inner lumen of a delivery catheter, the inner lumen having a proximal end and a distal end, the cover further configured to expand to an expanded configuration when advanced out of the distal end of the inner lumen of the delivery catheter and into the aneurysm, wherein the cover includes a diameter that is greater than the diameter or maximum transverse dimension of a neck portion of the aneurysm, and wherein the cover includes a distal concavity configured to face away from the neck portion of the aneurysm, and a first tubular mesh having a first end, a second end, a wall and a lumen, the first end and the second end of the first tubular mesh coupled to a central portion of the cover such that an intermediate portion of the first tubular mesh between the first end and the second end includes a substantially 180 degree turn, the intermediate portion of the first tubular mesh extending from the distal concavity of the cover, wherein the intermediate portion of the first tubular mesh has a collapsed configuration configured to be delivered through the inner lumen of the delivery catheter, and wherein the intermediate portion of the first tubular mesh is configured to expand to an expanded configuration when advanced out of the distal end of the inner lumen of the delivery catheter an into the aneurysm.

In another embodiment of the present disclosure, an apparatus for treating an aneurysm in a blood vessel includes an occlusion element configured to be releasably coupled to an elongate delivery shaft, the occlusion element including a cover having a mesh material and configured to be delivered in a collapsed configuration through an inner lumen of a delivery catheter, the inner lumen having a proximal end and a distal end, the cover further configured to expand to an expanded configuration when advanced out of the distal end of the inner lumen of the delivery catheter and into the aneurysm, wherein the cover includes a diameter that is greater than the diameter or maximum transverse dimension of a neck portion of the aneurysm, a first tubular mesh having a first end, a second end, a wall and a lumen, the first end and the second end of the first tubular mesh coupled to a central portion of the cover such that an intermediate portion of the first tubular mesh between the first end and the second end includes a substantially 180 degree turn, the intermediate portion of the first tubular mesh extending from the distal concavity of the cover, wherein the intermediate portion of the first tubular mesh has a collapsed configuration configured to be delivered through the inner lumen of the delivery catheter, and wherein the intermediate portion of the first tubular mesh is configured to expand to an expanded configuration when advanced out of the distal end of the inner lumen of the delivery catheter an into the aneurysm, and a second tubular mesh having a first end, a second end, a wall and a lumen, the first end and the second end of the second tubular mesh coupled to a central portion of the cover such that an intermediate portion of the second tubular mesh between the first end and the second end includes a substantially 180 degree turn, the intermediate portion of the second tubular mesh extending from the distal concavity of the cover, wherein the intermediate portion of the second tubular mesh has a collapsed configuration configured to be delivered through the inner lumen of the delivery catheter, and wherein the intermediate portion of the second tubular mesh is configured to expand to an expanded configuration when advanced out of the distal end of the inner lumen of the delivery catheter an into the aneurysm.

In yet another embodiment of the present disclosure, an apparatus for treating an aneurysm in a blood vessel includes an occlusion element configured to be releasably coupled to an elongate delivery shaft, the occlusion element including a cover having a mesh material and configured to be delivered in a collapsed configuration through an inner lumen of a delivery catheter, the inner lumen having a proximal end and a distal end, the cover further configured to expand to an expanded configuration when advanced out of the distal end of the inner lumen of the delivery catheter and into the aneurysm, wherein the cover in its expanded configuration has a transverse dimension that is greater than a maximum transverse dimension of a neck portion of the aneurysm, and a first tubular mesh having a first end, a second end, a wall and a lumen, the first end and the second end of the first tubular mesh coupled to a central portion of the cover such that an intermediate portion of the first tubular mesh between the first end and the second end includes a substantially 180 degree turn, the intermediate portion of the first tubular mesh extending distally from the central portion of the cover, wherein the intermediate portion of the first tubular mesh has a collapsed configuration configured to be delivered through the inner lumen of the delivery catheter, and wherein the intermediate portion of the first tubular mesh is configured to expand to an expanded configuration when advanced out of the distal end of the inner lumen of the delivery catheter an into the aneurysm.

In still another embodiment of the present disclosure, an apparatus for treating an aneurysm in a blood vessel includes an occlusion element configured to be releasably coupled to an elongate delivery shaft, the occlusion element including a first tubular mesh having a first end, a second end, a wall and a lumen, the first end and the second end of the first tubular mesh coupled together at a proximal end of the occlusion element such that an intermediate portion of the first tubular mesh between the first end and the second end includes a substantially 180 degree turn, the intermediate portion of the first tubular mesh extending distally from the proximal end of the occlusion element, wherein the intermediate portion of the first tubular mesh has a collapsed configuration configured to be delivered through the inner lumen of the delivery catheter, and wherein the intermediate portion of the first tubular mesh is configured to expand to an expanded configuration when advanced out of the distal end of the inner lumen of the delivery catheter an into the aneurysm. In some embodiments, the apparatus further includes a second tubular mesh having a first end, a second end, a wall and a lumen, the first end and the second end of the second tubular mesh coupled to the proximal end of the occlusion element such that an intermediate portion of the second tubular mesh between the first end and the second end includes a substantially 180 degree turn, the intermediate portion of the second tubular mesh extending distally from the proximal end of the occlusion element, wherein the intermediate portion of the second tubular mesh has a collapsed configuration configured to be delivered through the inner lumen of the delivery catheter, and wherein the intermediate portion of the second tubular mesh is configured to expand to an expanded configuration when advanced out of the distal end of the inner lumen of the delivery catheter an into the aneurysm.

DETAILED DESCRIPTION OF THE ILLUSTRATED EMBODIMENTS

Figure 1:
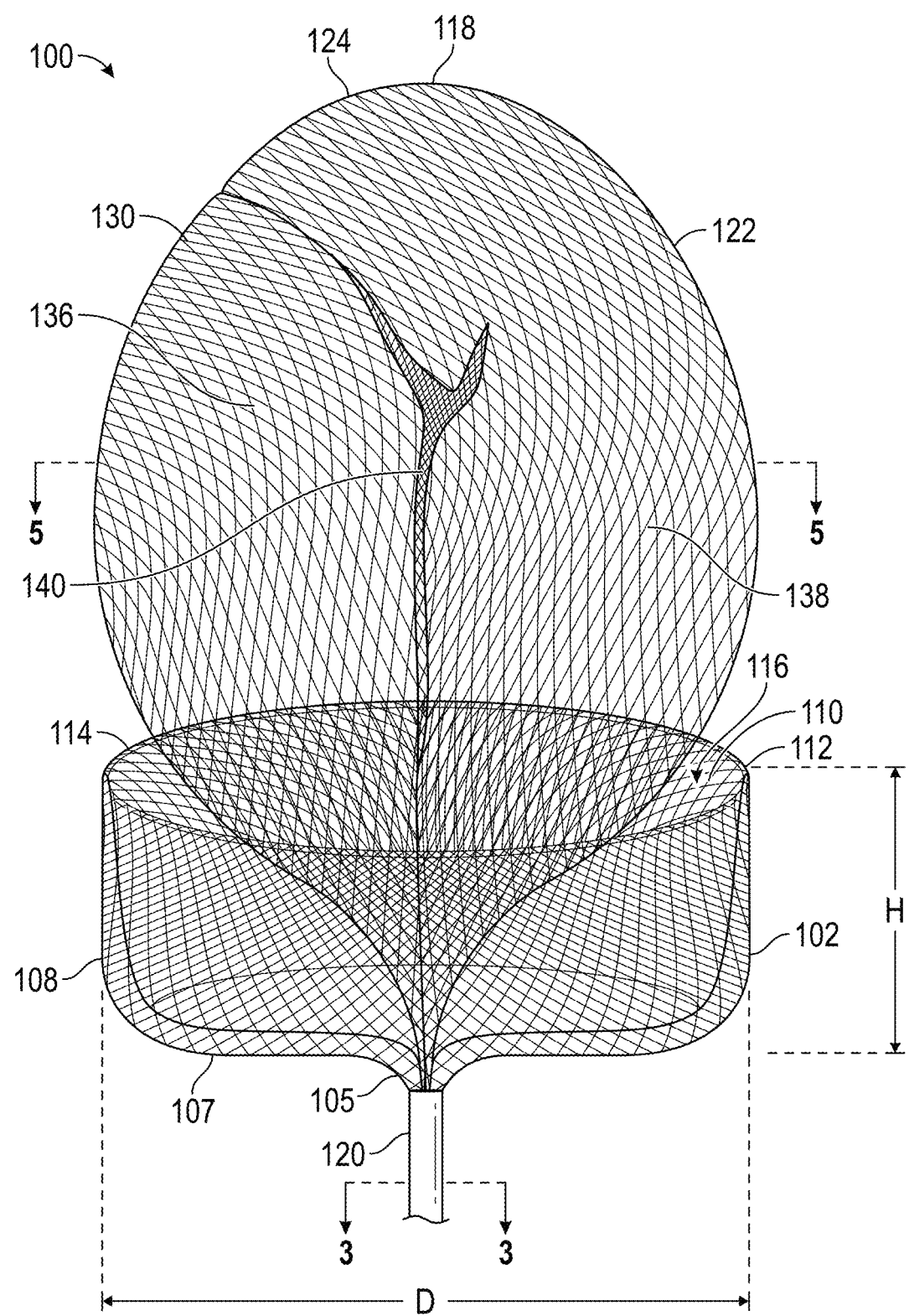
FIG. 1 is a perspective view of an occlusion device according to an embodiment of the present disclosure.

Aneurysms are abnormal bulging or weakening of a blood vessel, often an artery, and can have many complications. A bulging of the blood vessel can disrupt or put pressure on surrounding tissues. Cerebral aneurysms can result in a variety of side effects, such as impaired vision, impaired speech, impaired balance, etc. Further, the aneurysm creates a volume that is not along the main flow path of the blood through the blood vessel. It therefore can serve as a location for blood to become stagnant and, due to swirling eddy currents, can contribute to the formation of a thromboembolism. If an aneurysm ruptures, it can cause severe internal bleeding, which in cerebral arteries can often become fatal.

Aneurysms can be treated externally with open surgery. Such procedures typically involve closing off the entrance or "neck" of the aneurysm with a device such as vascular clip, clamp or a ligature. However, such open surgical procedures can be highly invasive and may lead to trauma to the adjacent tissue and other side effects.

Aneurysms can also be treated through endovascular procedures. In one procedure, detachable lengths of wires (e.g., coils) are inserted into the interior volume of the aneurysm using a catheter. The coils are intended to fill the volume of the aneurysm to decrease the flow of blood into the aneurysm, inducing stagnation of flow and stimulate clotting within the aneurysm. In settings of large cerebral aneurysms, filling of the aneurysm with multiple coils can lead to mass effect that may induce brain swelling and be an independent cause for new symptoms. In another procedure, for aneurysms with a relatively large neck, the adjunctive use of stents assists with the retention of the coils within the aneurysm. This approach may have a contraindication to being used when treating ruptured aneurysm, due to the need for additional anti-thrombotic medications. In another procedure, the coils are held in the volume of the aneurysm with a temporary balloon that is inflated in the blood vessel. The balloon is deflated and removed once the mass of coils is secured. In still another procedure, a stent device is placed in the artery to promote flow of blood past the aneurysm. This leads to stagnation of the blood within the aneurysm and thrombosis inside the aneurysm volume. However, a side branch of a main artery in which the stent device is placed may become trapped or "jailed," which can impede access to the side branch. In other instances, the side branch can become clotted off, possibly causing a stroke. Additionally, such a procedure generally requires the use additional anti-thrombotic medications, which limits the use of such devices in the setting of treatment of ruptured aneurysms. The stent device is often formed with a relatively tight weave. While the tight weave increases the effectiveness of the stent device in diverting the blood flow, it also impedes or prevents access to the volume of the aneurysm or the jailed artery. In the event that the aneurysm fails to clot, the obstruction of the aneurysm by the stent device prevents the possibility of placing embolic devices inside the aneurysm. Additional procedures such as the placement of additional stents or open surgery may then be required to treat the residual.

Procedures that involve packing the volume of the aneurysm can suffer from several common shortcomings. First, it can take many coils of wire to fill the volume of the aneurysm, which is time consuming and increases the time it takes to complete the procedure. Further, the coils may be compacted over time to occupy a smaller percentage of the total volume of the aneurysm. A great enough compaction of the coils can be considered a recurrence of the aneurysm and may require further treatment.

FIG. 1 illustrates an occlusion device 100 configured for placement within an aneurysm. The occlusion device 100 comprises a cover 102 having an outer diameter D. In some embodiments, the cover 102 is circular, with substantially the same diameter D at any transverse measurement around the perimeter. In other embodiments, the cover 102 is non-circular, and may comprise an ellipse, an oval, a polygon or other shapes. In the non-circular embodiments, the cover 102 comprises a minimum transverse dimension and a maximum transverse dimension. In the particular case of an ellipse or an oval shape, the cover 102 comprises a major diameter and a minor diameter. The minor diameter or minimum transverse dimension is configured to be larger than a maximum transverse dimension of an opening into the aneurysm (the neck portion). Thus, the cover 102 is configured to completely cover the neck portion, and thus to cause stagnation of blood within the aneurysm, leading to occlusion. The cover 102 is constructed from a mesh (braided) Nitinol (nickel-titanium alloy) tube 105 that is inverted on itself. The mesh tube 105 has a first end 104 and a second end 106 (see FIG. 3). The second end 106 is folded back over the outer diameter of the first end 104 thus providing an outer facing surface 108 and an inner facing surface 110. The mesh tube 105 is heat-formed such that cover 102 comprises an expanded portion and the first end 104 and second end 106 comprise unexpanded (or partially expanded) portions. A smooth fold 112 extends around the circumference 114 of the cover 102 and represents the transition between the outer facing surface 108 and the inner facing surface 110. The fold 112 avoids any sharp edge that might risk rupture of an aneurysm wall, or other anatomical damage. The cover 102 includes a concavity 116 facing toward the distal end 118 of the occlusion device 100 and away from the proximal end 120 of the occlusion device 100. The cover 102 is fabricated as an inverted mesh tube 105 having a simple straight elongate configuration, and is subsequently formed into the shape shown in FIG. 1, and heat set into this shape. For example, the inverted mesh tube 105 may be constructed as a single layer mesh tube formed of at least some nickel-titanium alloy filaments, and then inverted on itself. The inverted mesh tube 105 may then be placed into a die or mold comprising one or more pieces, to hold it in the shape of the cover 102. Then, the cover 102 may be subjected to an elevated temperature and then cooled, to lock in the shape, resulting in a cover 102 having at least some superelastic properties. The cover 102 includes a lower portion 107 opposite the fold 112. The lower portion 170 is substantially flat, generally defining a plane, but in other embodiments may have a more frustoconical or hemispheric shape.

Figure 2:
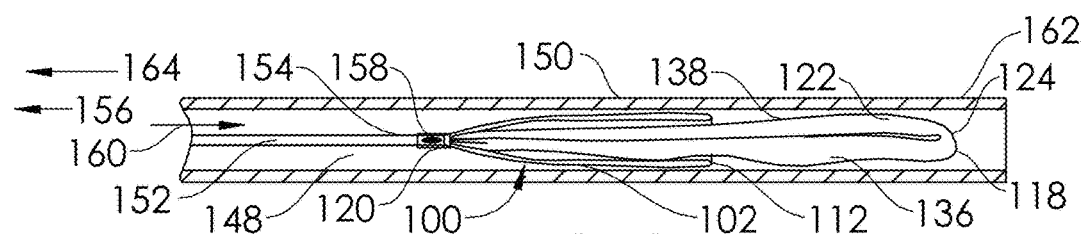
FIG. 2 is a sectional view of the occlusion device of FIG. 1 within a delivery catheter.

As formed (e.g., heat-formed), the cover 102 has an expanded configuration (shown in FIG. 1) and a collapsed configuration, shown in FIG. 2. The cover 102 comprises two mesh layers, provided by the outer facing surface 108 and the inner facing surface 110. In some embodiments, the cover 102 may comprise some nickel-titanium alloy filaments and some radiopaque elements, comprising platinum, gold, tantalum, or alloys of any of these or other radiopaque materials. In some embodiments, the filaments may comprise drawn filled tubes (DFT), such as those comprising a nickel-titanium alloy outer wall and a platinum core. The radiopaque material allows the cover 102 to be visible on radiographs or fluoroscopy. The occlusion device 100 may be configured by controlling how much radiopaque material is used, by either the ratio of radiopaque filaments to non-radiopaque filaments, or by the amount of platinum core in the drawn filled tubes. In this manner, the cover 102 can be selectively fabricated to be sufficiently visible, but not over visible, e.g., overly bright, such that other objects are obscured. In some embodiments, whether any of the filaments comprise radiopaque materials or not, a marker band may be attached to the proximal end 120 of the occlusion device 100, by adhesive or epoxy bonding, or swaging, welding or other mechanical attachment.

Figure 3:
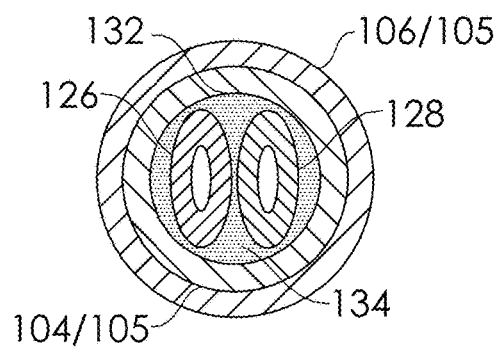
FIG. 3 is a cross-sectional view of the occlusion device of FIG. 1 taken through line 3-3.
Figure 4:
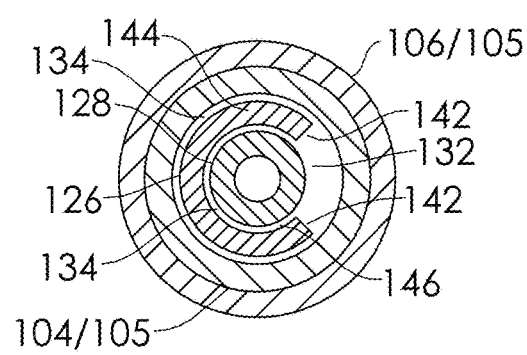
FIG. 4 is a cross-sectional view of an alternative embodiment of the present disclosure.

Extending from the concavity 116 is a doubled-over or looped tubular mesh 122 having a smooth apex 124 configured to safely contact an interior wall of an aneurysm. The tubular mesh 122 has a first end 126 and a second end 128, and an intermediate portion 130 extending between the first end 126 and second end 128. In the embodiment shown in FIG. 1, the first end 126 and second end 128 are substantially unexpanded and are inserted within a lumen 132 within the inverted mesh tube 105 that forms the cover 102, particularly at the first end 104 and a second end 106 of the mesh tube 105 that forms the cover 102 (FIG. 3). The first end 126 and second end 128 of the tubular mesh 122 can be bonded into the lumen 132 with adhesive 134, or alternatively with epoxy, or welded or bonded with any other securement technique. The first end 126 and second end 128 may each be compressed or deformed into an oval, elliptical, or D-shape, so that they may more efficiently fit into a circular cross-section of the lumen 132. An alternative configuration is shown in FIG. 4, wherein the first end 126 includes a cut 142 in its wall 144, which allows the second end 128 to be inserted into the internal space 146 at the first end 126. Thus, the second end 128 is held within the first end 126, and the first end 126 and second end 128 are secured within the lumen 132, e.g., with adhesive, epoxy, welding or other securing techniques. The tubular mesh 122 is constructed from a mesh (braided) Nitinol (nickel-titanium alloy) tube, and may also include filaments of platinum or other radiopaque materials, as well as the nickel-titanium alloy filaments. Drawn filled tubes may also be utilized.

Figure 5:
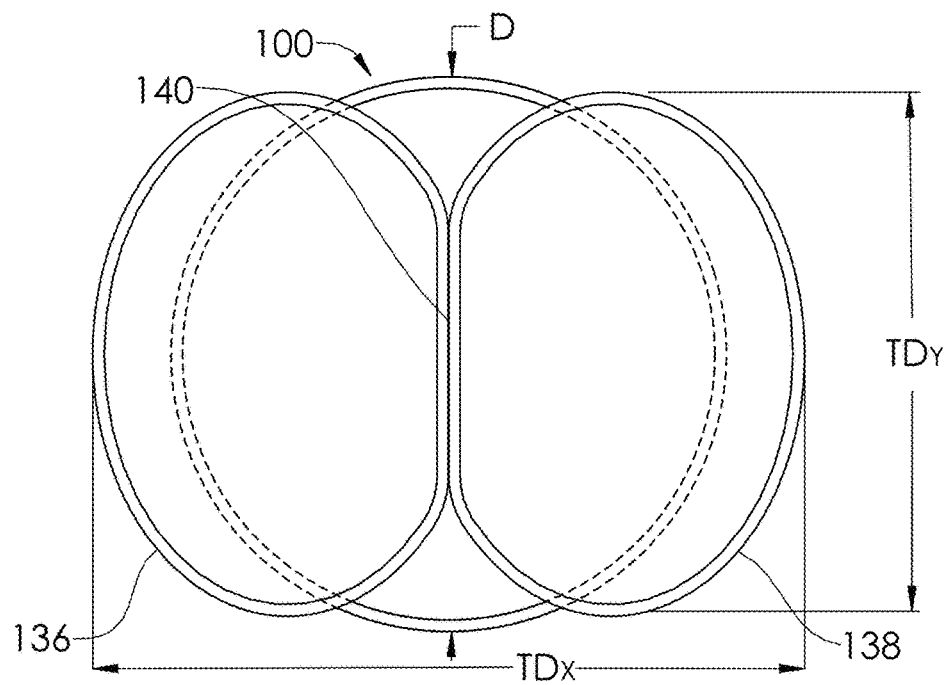
FIG. 5 is a cross-sectional view of the of the occlusion device of FIG. 1 taken through line 5-5.

Between the apex 124 of the intermediate portion 130 and the first and second ends 126, 128, the tubular mesh 122 intermediate portion 130 also comprises a first leg 136 and a second leg 138, extending therefrom. Each of the first leg 136 and second leg 138 comprises a different section of the tubular mesh 122. Thus, the tubular mesh 122 is a single layer mesh (braided) tube extending from its first end 126 through the first leg 136 and around the apex 124, then through the second leg 138 to the second end 128. In the embodiment shown in FIG. 1, the first leg 136 and second leg 138 are shown in their substantially unrestrained, expanded states, and, in this embodiment, the first leg 136 and second leg 138 each have a large enough diameter such that they contact each other at a central axis 140. Turning to FIG. 5, it can be appreciated that the first leg 136 and second leg 138 each form a more oval or elliptical cross-sectional shape, rather than a circular shape, because of their opposition to each other at the central axis 140. Also, the first leg 136 and second leg 138 together form a first transverse dimension $TD_X$ and a second transverse dimension $TD_Y$. In this embodiment, the first transverse dimension $TD_X$ is greater than the second transverse dimension $TD_Y$. In other embodiments, the first transverse dimension $TD_X$ is less than the second transverse dimension $TD_Y$. In some embodiments, the first transverse dimension $TD_X$ is equal to the second transverse dimension $TD_Y$. In some cases, the first transverse dimension $TD_X$ is configured to contact an interior wall of an aneurysm, to stabilize the occlusion device 100 within the aneurysm, while the second transverse dimension $TD_Y$ is not. In some cases, the second transverse dimension $TD_Y$ is configured to contact an interior wall of an aneurysm, to stabilize the occlusion device 100 within the aneurysm, while the first transverse dimension $TD_X$ is not. In some cases, the occlusion device 100 may be placed into a non-circular aneurysm, and in these cases, the first transverse dimension $TD_X$ and the second transverse dimension $TD_Y$ may each be configured to contact an interior wall of an aneurysm at different circumferential locations, as the aneurysmal cross-section may be more oval or elliptical, or another non-circular shape.

Returning to FIG. 2, the occlusion device 100 is shown with both the cover 102 and the tubular mesh 122 in their collapsed or compacted configurations while it is placed into the lumen 148 of a delivery catheter 150 having a distal end 162 and a proximal end 164. The delivery catheter 150 may be a microcatheter having a luminal diameter of 0.017 inch or 0.021 inch, 0.025 inch, or 0.028 inch, or other sizes. An elongate pusher 152, having a distal end 154 and a proximal end 156, may comprise a wire, a hypo tube, or another elongate structure having column support, and is detachably coupled at its distal end 154 to the proximal end 120 of the occlusion device 100. A detachable joint 158 may comprise one of a number of detachment systems, including but not limited to pressurized detachment, electrolytic detachment mechanisms, hydraulic detachment mechanisms, mechanical or interlocking detachment mechanisms, chemical detachment mechanisms, heat-activated detachment systems, or frictional detachment systems. In any of the embodiments disclosed herein, alternative detachable joint may be employed, such as the detachable joints disclosed in co-pending U.S. patent application Ser. No. 16/840,410, filed on Apr. 5, 2020, and entitled "Systems and Methods for Treating Aneurysms" and in co-pending U.S. patent application Ser. No. 16/840,412, filed on Apr. 5, 2020, and entitled "Systems and Methods for Treating Aneurysms," both of which are hereby incorporated by reference in their entirety for all purposes. During delivery, the pusher 152 is held on its proximal end 156 by a user and pushed in a forward longitudinal direction 160, in order to advance the occlusion device 100 to the distal end 162 of the delivery catheter 150.

Figure 6:
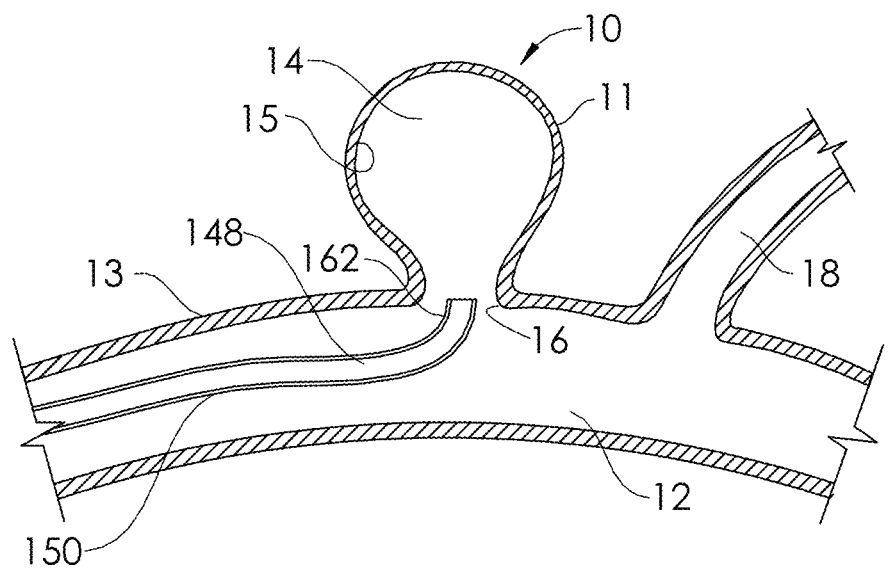
FIGS. 6-9 illustrate the implantation of the occlusion device of FIG. 1 in an aneurysm of a blood vessel of a patient.

In FIGS. 6-9, an aneurysm 10 having a neck portion 16 is shown. The occlusion device 100 is shown in use being implanted by a user (e.g., physician) into the aneurysm 10 through the delivery catheter 150 to disrupt or halt the flow of blood flow between the blood vessel 12 and the internal volume 14 of the aneurysm 10, thereby reducing the likelihood that the aneurysm 10 will rupture. Or, in cases in which the aneurysm 10 has already ruptured, the occlusion device 100 is being implanted to help heal the rupture and/or to prevent rerupture. The occlusion device 100 is configured to be low profile device, minimizing disruptions to surrounding bodies, such as a side branch 18 of the blood vessel 12. The blood vessel 12 has a blood vessel wall 13 and the aneurysm 10 has an aneurysm wall 11. In FIG. 6, the delivery catheter 150 is advanced through a sheath and/or guiding catheter (not shown) through a puncture or cutdown in a peripheral blood vessel, such as a femoral artery, a brachial artery, or a radial artery. The distal end 162 of the delivery catheter 150 may be shaped with a curve, as shown, either by the manufacturer, or prior to the procedure by the user, in order to allow for improved backup support when delivering the occlusion device 100, as well as to aid deliverability into the aneurysm 10. The distal end 162 of the delivery catheter 150 is placed adjacent the neck portion 16 of the aneurysm 10. The delivery catheter 150 may first be advanced over a guidewire (not shown) that is passed through the lumen 148. The guidewire may then be removed, leaving the lumen 148 as a delivery conduit and the delivery catheter 150 as a support column.

Figure 7:
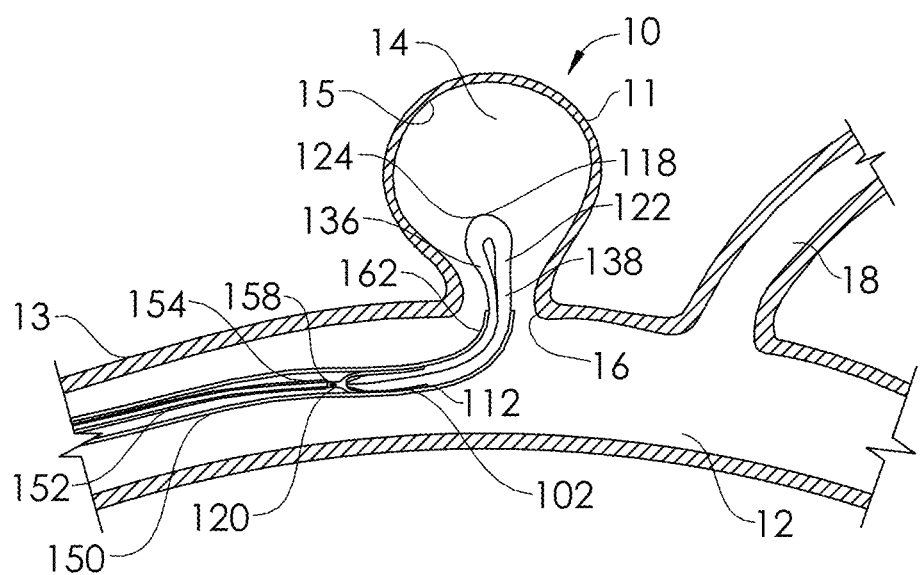
Figure 8:
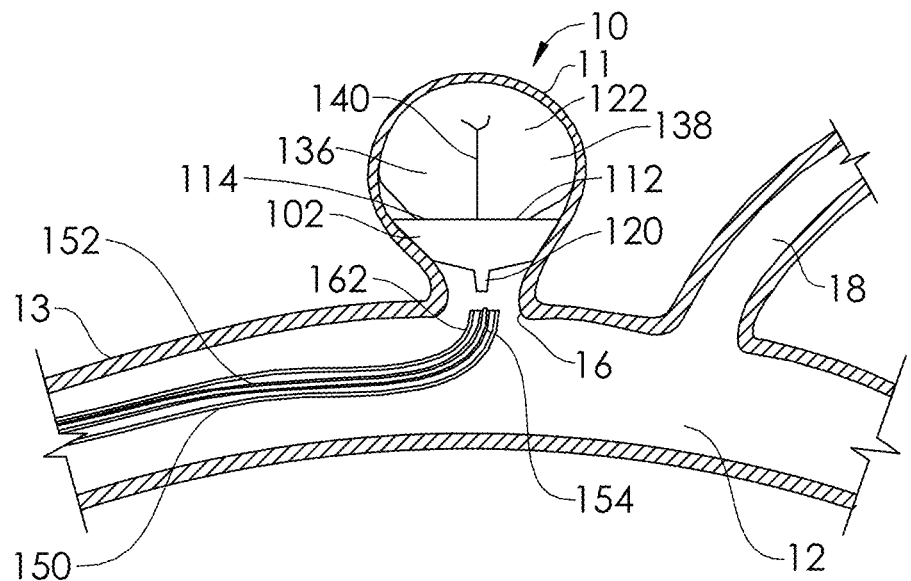

In FIG. 7, the occlusion device 100 is advanced through the lumen 148 of the delivery catheter 150, as described, and the distal end 118 of the occlusion device 100, having a smooth apex 124 (of a curve in the tubular mesh 122) is advanced out of the lumen 148 and into the internal volume 14 of the aneurysm 10. The smooth apex 124 is the first portion of the occlusion device 100 that exits the lumen 148 and thus is the first portion of the occlusion device to enter the aneurysm 10. The smooth apex 124, because of is curved and contoured surface as well as its flexible mesh wall, is a blunt, soft, and atraumatic element that is configured to first contact the interior surface 15 of the aneurysm 10. The smooth apex 124 can contact the interior surface 15 and slide around the interior surface 15 is a less traumatic manner than most devices that are configured to implant into an aneurysm, such as small diameter detachable coils. The atraumatic characteristics of the smooth apex 124 make it fully deployable not only in unruptured cerebral aneurysms, but also in ruptured cerebral aneurysms, where certain other devices may be contraindicated. In FIG. 8, the occlusion device 100 is shown in a substantially expanded configuration within the internal volume 14 of the aneurysm 10. The cover 102 is expanded against the interior surface 15 of the aneurysm 10, and covers the neck portion 16 of the aneurysm. The tubular mesh 122 is expanded against the interior surface 15 of the aneurysm 10, at least at one or more portions, and serves to anchor or stabilize the cover 102 in the aneurysm 10 and adjacent the neck portion 16.

Figure 9:
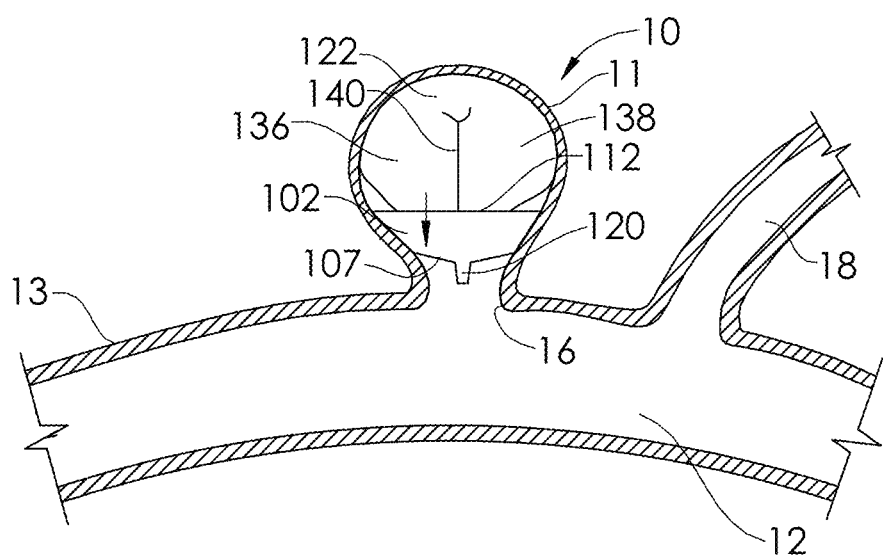

Also, in FIG. 8, the detachable joint 158 has been detached, and thus, the free end 154 of the pusher 152 can be pulled into the lumen 148 of the delivery catheter 150. In some embodiments, the delivery catheter 150 is maintained over the detachable joint 158 during the detachment procedure, to further protect the aneurysm 10. In FIG. 9, the delivery catheter 150 is removed, and the deployed occlusion device 100 is in place to begin to occlude the internal volume 14 of the aneurysm 10. The expanded tubular mesh 122 also serves to force the cover 102 against the neck portion 16 and/or against the interior surface 15, see straight arrow in FIG. 9. The dual layers of mesh in the cover 102 at the lower portion 107 (FIGS. 1 and 9) aid in the disruption of blood flow into the aneurysm 10, thus causing thrombosis to isolate the internal volume 14 of the aneurysm 10 from blood flow through the blood vessel. 12. The force (straight arrow) maintaining the cover 102 in place further assures this process, and also protects against undesired compaction over time of the occlusion device 100, whether it be compaction in the longitudinal direction or compaction in a transverse or radial direction.

Figure 10:
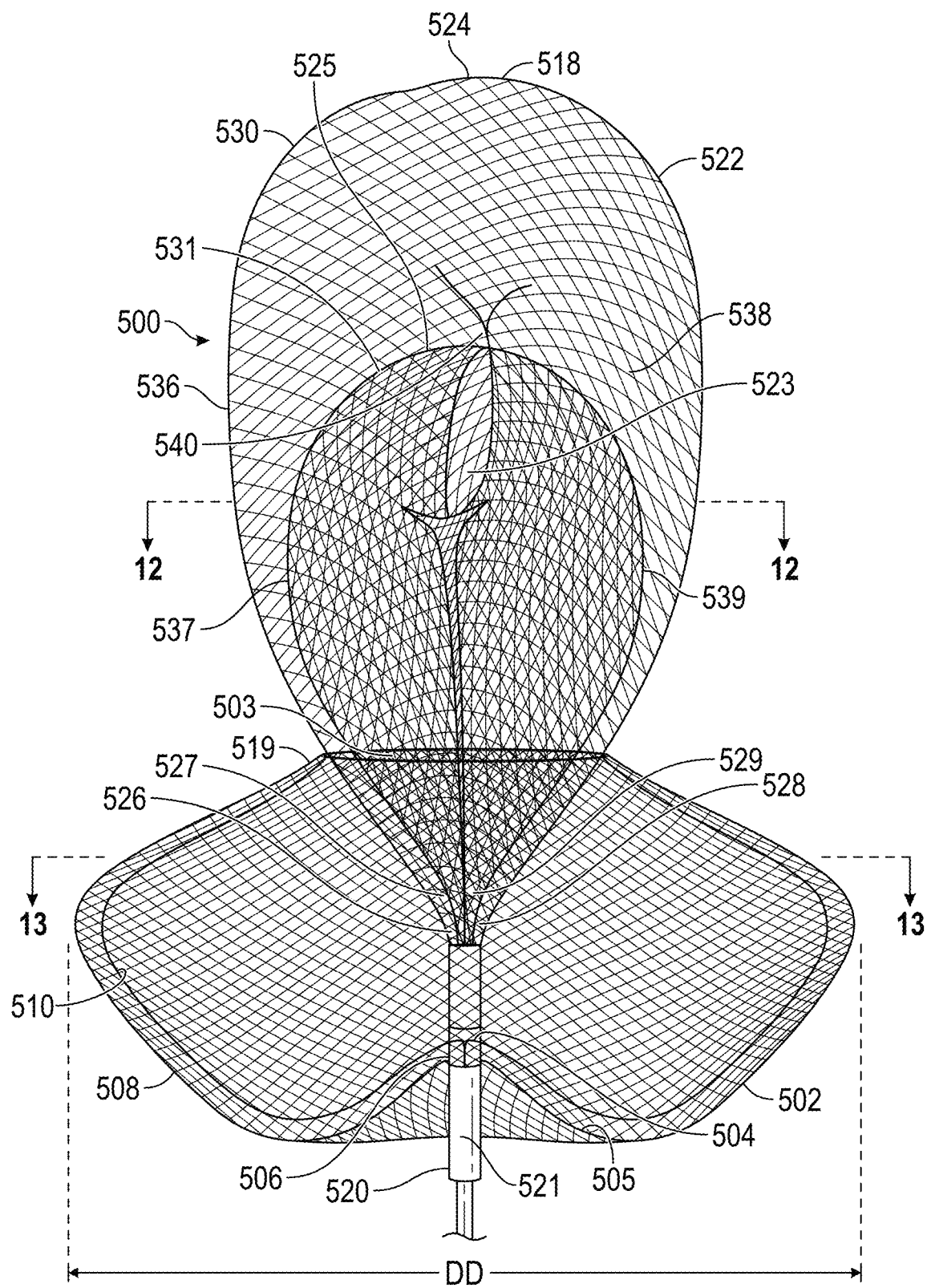
FIG. 10 is a perspective view of an occlusion device according to an alternative embodiment of the present disclosure.
Figure 13:
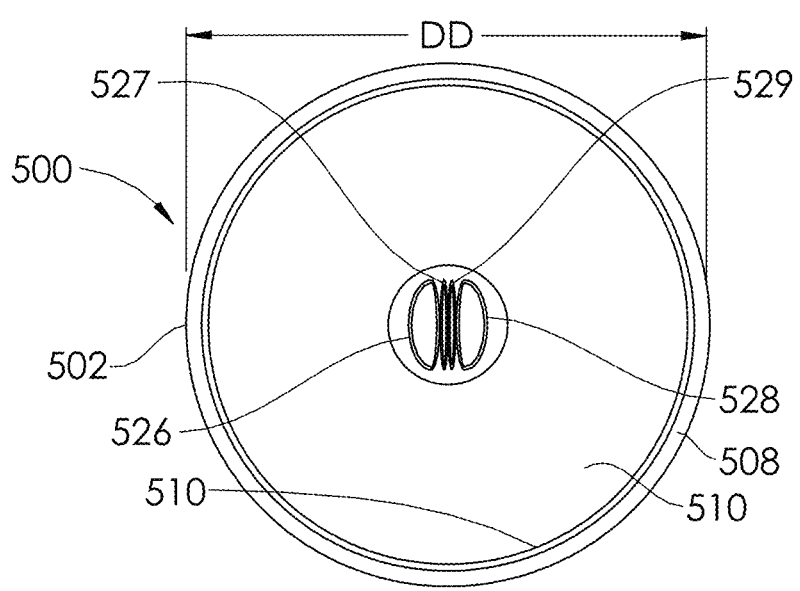
FIG. 13 is a cross-sectional view of the of the occlusion device of FIG. 10 taken through line 13-13.

FIG. 10 illustrates an occlusion device 500 configured for placement within an aneurysm. The occlusion device 500 is an alternative configuration of the occlusion device 100 of FIG. 1, comprises a cover 502 having an outer diameter DD. In some embodiments, the cover 502 is circular, with substantially the same diameter DD at any measurement around the perimeter at each transverse plane. In other embodiments, the cover 502 is non-circular, and may comprise a cross-section having an ellipse, an oval, a polygon or other shapes. In the non-circular embodiments, the cover 502 comprises a minimum transverse dimension and a maximum transverse dimension. In the particular case of an ellipse or an oval shape, the cover 502 comprises a major diameter and a minor diameter. The minor diameter or minimum transverse dimension is configured to be larger than a maximum transverse dimension of an opening into the aneurysm (the neck portion). Thus, the cover 502 is configured to completely cover the neck portion, and thus to cause stagnation of blood within the aneurysm, leading to occlusion. The cover 502 is constructed from a mesh (braided) Nitinol (nickel-titanium alloy) tube 505 that is inverted on itself. The mesh tube 505 has a first end 504 and a second end 506 (FIG. 11), similar to the first end 104 and second end 106 of FIG. 3. The second end 506 is folded back over the outer diameter of the first end 504 thus providing an outer facing surface 508 and an inner facing surface 510 (FIG. 13). The mesh tube 505 is heat-formed such that cover 502 comprises an expanded portion and the first end 504 and second end 506 comprise unexpanded (or partially expanded) portions. The heat forming may be done as described in relation to the occlusion device 100 of FIG. 1. The cover 502 has a general disk shape defined by the outer facing surface 508. In some embodiments, the cover 502 may comprise a toroidal, partially-toroidal shape. The occlusion device 500 includes a distal end 518 and a proximal end 520. As formed (e.g., heat-formed), the cover 502 has an expanded configuration (shown in FIG. 10) and a collapsed configuration, shown in FIG. 11. The cover 502 comprises two mesh layers, provided by the outer facing surface 508 and the inner facing surface 510. In some embodiments, the cover 502 may comprise some nickel-titanium alloy filaments and some radiopaque elements, comprising platinum, gold, tantalum, or alloys of any of these or other radiopaque materials. In some embodiments, the filaments may comprise drawn filled tubes (DFT), such as those comprising a nickel-titanium alloy outer wall and a platinum core. The radiopaque material allows the cover 502 to be visible on radiographs or fluoroscopy. The occlusion device 500 may be configured by controlling how much radiopaque material is used, by either the ratio of radiopaque filaments to non-radiopaque filaments, or by the amount of platinum core in the drawn filled tubes. In this manner, the cover 502 can be selectively fabricated to be sufficiently visible, but not over visible, e.g., overly bright, such that other objects are obscured. In some embodiments, whether any of the filaments comprise radiopaque materials or not, a marker band 521 may be attached to the proximal end 520 of the occlusion device 500, by adhesive or epoxy bonding, or swaging, welding or other mechanical attachment.

Extending from an opening 503 in a distal portion 519 the cover 502 is a first doubled-over or looped tubular mesh 522 and a second doubled-over or looped tubular mesh 523. The first looped tubular mesh 522 has a smooth apex 524 configured to safely contact an interior wall of an aneurysm. The second looped tubular mesh 523 has an apex 525 configured to fit within a central axis 540 of the first tubular mesh 522. The first tubular mesh 522 and the second tubular mesh 523 are oriented at non-parallel planes to one another. A shown in FIG. 12, in one embodiment, the first tubular mesh 522 and the second tubular mesh 523 are orthogonal to each other, and substantially follow orthogonal planes, or planes at right angles to one another. The first tubular mesh 522 has a first end 526 and a second end 528, and an intermediate portion 530 extending between the first end 526 and second end 528. In the embodiment shown in FIG. 10, the first end 526 and second end 528 are substantially unexpanded and are inserted within a lumen (not shown) within the inverted mesh tube 505 that forms the cover 502, in a similar manner to the first end 104 and the second end 106 in FIG. 3. Similarly, the second tubular mesh 523 has a first end 527 and a second end 529, and an intermediate portion 531 extending between the first end 527 and second end 529. In the embodiment shown in FIG. 10, the first end 527 and second end 529 are substantially unexpanded and are inserted within a lumen (not shown) within the inverted mesh tube 505 that forms the cover 502. The first ends 526, 527 and second ends 528, 529 of the first tubular meshes 522, 523 can be bonded into the lumen with adhesive, or alternatively with epoxy, or welded or bonded with any other securement technique. The first ends 526, 527 and second ends 528, 529 may each be compressed or deformed into an oval, elliptical, or D-shape, so that they may more efficiently fit into a circular cross-section of the lumen. The alternative configuration of FIG. 4 may also be employed. The first tubular mesh 522 and second tubular mesh 523 may each be constructed from a mesh (braided) Nitinol (nickel-titanium alloy) tube, and may also include filaments of platinum or other radiopaque materials, as well as the nickel-titanium filaments. Drawn filled tubes may also be utilized.

Figure 12:
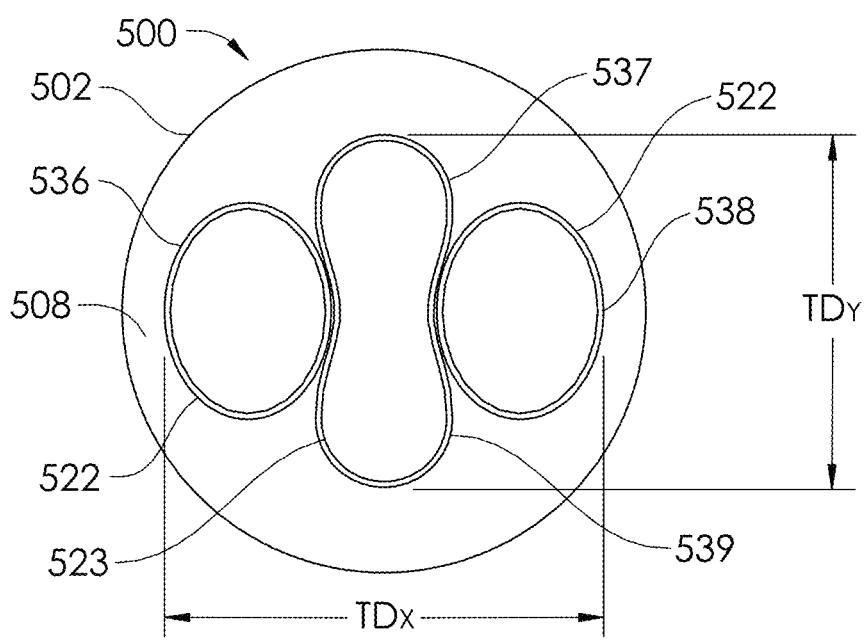
FIG. 12 is a cross-sectional view of the of the occlusion device of FIG. 10 taken through line 12-12.

Between the apex 524 of the intermediate portion 530 and the first and second ends 526, 528, the tubular mesh 522 intermediate portion 530 also comprises a first leg 536 and a second leg 538, extending therefrom. Between the apex 525 of the intermediate portion 531 and the first and second ends 527, 528, the tubular mesh 523 intermediate portion 531 also comprises a first leg 537 and a second leg 539, extending therefrom. In the embodiment shown in FIG. 10, the first legs 536, 537 and the second leg 538, 539 are shown in their expanded states. Turning to FIG. 12, the spacing between the first leg 536, first leg 537, second leg 538, and second leg 539 can be appreciated. Each leg 536, 537, 538, 539 may form a circular cross-sectional shape when expanded, or may form a more oval or elliptical cross-sectional shape, because of their opposition to or interface with each other. Each leg pair 536/538, 537/539 may form a first transverse dimension $TD_X$ and a second transverse dimension $TD_Y$, respectively (see FIG. 12). For example, in some embodiments, the first transverse dimension $TD_X$ may be greater than the second transverse dimension $TD_Y$. In some embodiments, the first transverse dimension $TD_X$ may be less than the second transverse dimension $TD_Y$. In some embodiments, the first transverse dimension $TD_X$ is configured to contact an interior wall of an aneurysm, to stabilize the occlusion device 500 within the aneurysm, while the second transverse dimension $TD_Y$ is not. In some embodiments, the second transverse dimension $TD_Y$ is configured to contact an interior wall of the aneurysm, while the first transverse dimension $TD_X$ is not. In some embodiments, both the first transverse dimension $TD_X$ and the second transverse dimension $TD_Y$ are configured to contact an interior wall of the aneurysm. The cover 502 may alternatively have a distal concavity, like the cover 102 of the occlusion device 100 of FIG. 1. Furthermore, the cover 102 of the occlusion device 100 of FIG. 1 may utilize a cover 502 without a distal concavity, and instead with an opening 503, as in the occlusion device 500 of FIG. 10.

Figure 11:
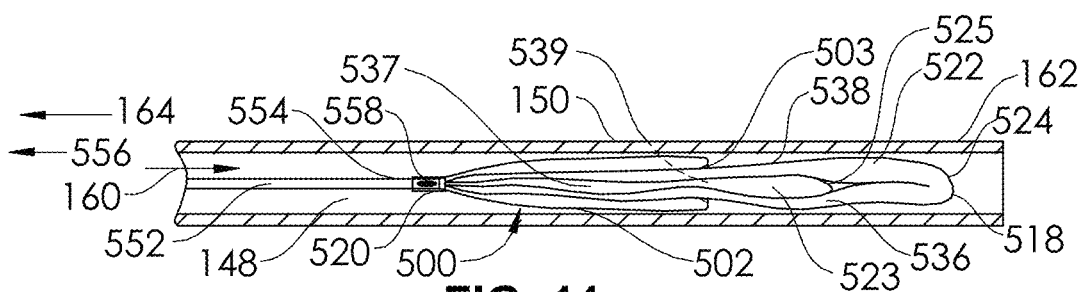
FIG. 11 is a sectional view of the occlusion device of FIG. 10 within a delivery catheter.

Turning to FIG. 11, the occlusion device 500 is shown with both the cover 502 and the tubular meshes 522, 523 in their collapsed or compacted configurations while it is placed into the lumen 148 of a delivery catheter 150 having a distal end 162 and a proximal end 164. The delivery catheter 150 may be a microcatheter having a luminal diameter of 0.017 inch or 0.021 inch, 0.025 inch, or 0.028 inch, or other sizes. An elongate pusher 552, having a distal end 554 and a proximal end 556, may comprise a wire, a hypo tube, or another elongate structure having column support, and is detachably coupled at its distal end 554 to the proximal end 520 of the occlusion device 500. A detachable joint 558 may comprise one of a number of detachment systems, including but not limited to pressurized detachment, electrolytic detachment mechanisms, hydraulic detachment mechanisms, mechanical or interlocking detachment mechanisms, chemical detachment mechanisms, heat-activated detachment systems, or frictional detachment systems. During delivery, the pusher 552 is held on its proximal end 556 by a user and pushed in a forward longitudinal direction 160, in order to advance the occlusion device 500 to the distal end 162 of the delivery catheter 150.

Figure 14:
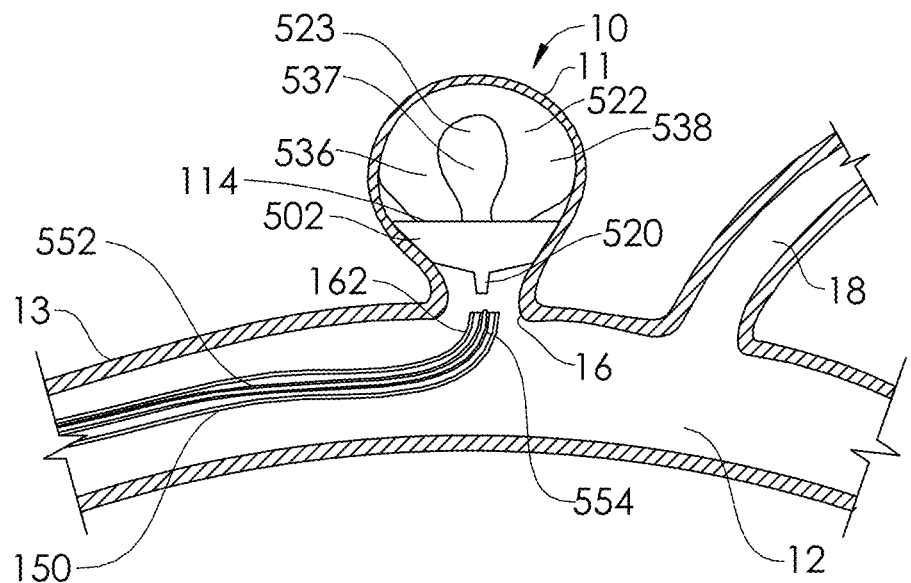
FIGS. 14-15 illustrate the implantation of the occlusion device of FIG. 10 in an aneurysm of a blood vessel of a patient.
Figure 15:
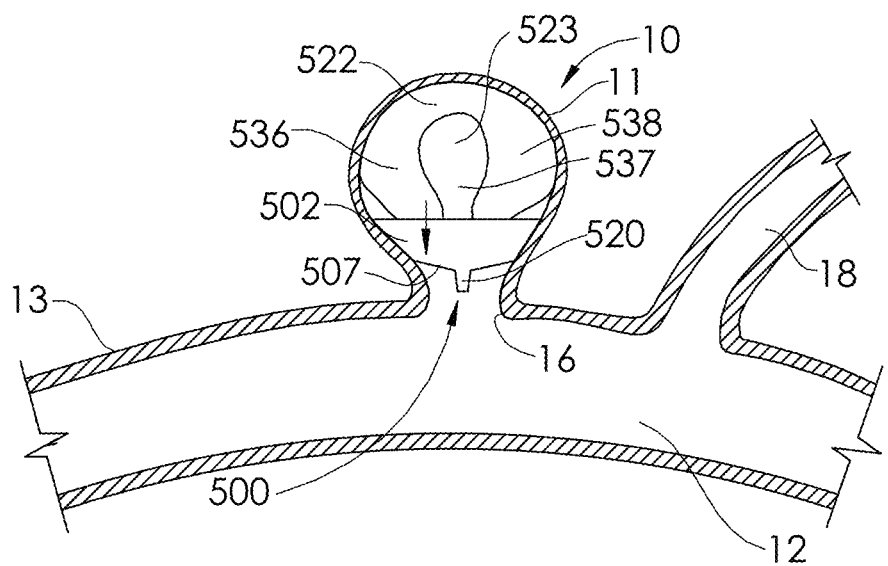

In FIG. 14, the occlusion device 500 is shown in a substantially expanded configuration within the internal volume 14 (see FIG. 6) of the aneurysm 10. The cover 502 is expanded against the interior surface 15 of the aneurysm 10, and covers the neck portion 16 of the aneurysm. One or both of the first tubular mesh 522 and the second tubular mesh 523 are expanded against the interior surface 15 (see FIG. 6) of the aneurysm 10, and serve(s) to anchor or stabilize the cover 502 in the aneurysm 10 and adjacent the neck portion 16. Also, in FIG. 14, the detachable joint 558 has been detached, and thus, the free end 554 of the pusher 552 can be pulled into the lumen 148 of the delivery catheter 150. In some embodiments, the delivery catheter 150 is maintained over the detachable joint 558 during the detachment procedure, to further protect the aneurysm 10. In FIG. 15, the delivery catheter 150 is removed, and the deployed occlusion device 500 is in place to begin to occlude the internal volume 14 of the aneurysm 10. The expanded first tubular mesh 522 and expanded second tubular mesh 523 also serve to force the cover 502 against the neck portion 16 and/or against the interior surface 15, see straight arrow in FIG. 15. The dual layers of mesh in the cover 502 at a lower portion 507 aid in the disruption of blood flow into the aneurysm 10, thus causing thrombosis to isolate the internal volume 14 of the aneurysm 10 from blood flow through the blood vessel. 12. The force (straight arrow) maintaining the cover 502 in place further assures this process, and also protects against undesired compaction over time of the occlusion device 500.

Figure 16:
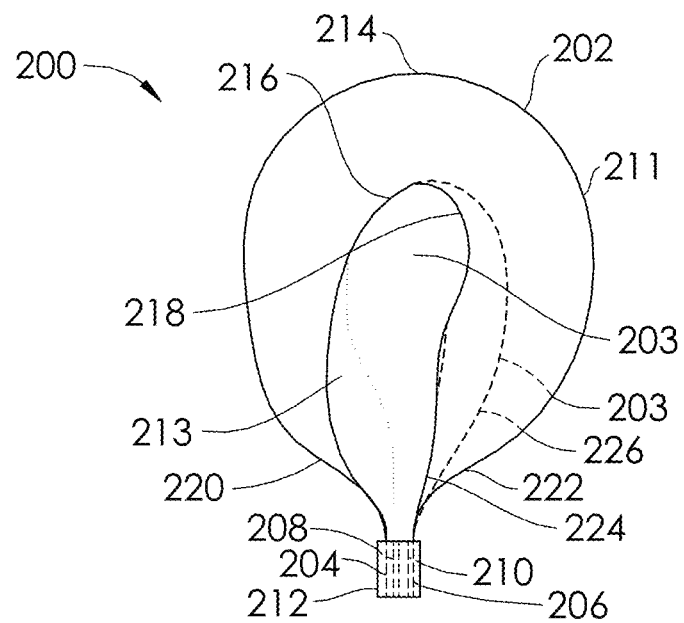
FIG. 16 is a perspective view of an occlusion device according to an alternative embodiment of the present disclosure.

FIG. 16 illustrates an occlusion device 200 comprising a first doubled-over or looped tubular mesh 202 and a second doubled-over or looped tubular mesh 203. The occlusion device 200 is similar to the occlusion device 500 of FIG. 10, however there is no cover (e.g., cover 502). The first tubular mesh 202 includes a first end 204 and a second end 206, and the second tubular mesh has a first end 208 and a second end 210. All four ends 204, 206, 208, 210 are held, in the collapsed or constrained configuration of the tubular mesh 202, 203, within a cylindrical marker band 212. The marker band 212 may comprise stainless steel or a radiopaque material such as platinum, and the ends 204, 206, 208, 210 may be bonded within a lumen of the marker band 212 with adhesive or epoxy, or may be brazed, soldered, or welded. The first looped tubular mesh 202 has an intermediate portion 211 having a smooth apex 214 configured to safely contact an interior wall of an aneurysm. The second looped tubular mesh 203 has an intermediate portion 213 having an apex 216 configured to fit within a central axis 218 of the first tubular mesh 202. The first tubular mesh 202 and the second tubular mesh 203 are oriented at non-parallel planes to one another. A shown in FIG. 16, the first tubular mesh 202 and the second tubular mesh 203 are substantially orthogonal to each other, and substantially follow orthogonal planes, or planes at right angles to one another. Because there is no cover, a first proximal portion 220 and second proximal portion 222 of the first tubular mesh 202, and a first proximal portion 224 and second proximal portion 226 of the second tubular mesh 203 are shaped and configured to serve (as did the cover 502) to be disposed against the proximal portion of an aneurysm, adjacent the neck of the aneurysm, to substantially provide occlusion of the neck.

Figure 17:
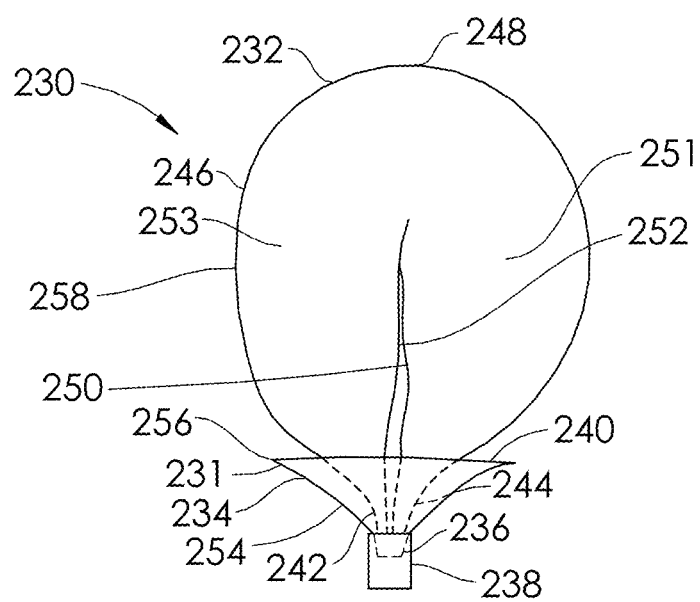
FIG. 17 is a perspective view of an occlusion device according to an alternative embodiment of the present disclosure.

FIG. 17 illustrates an occlusion device 230 comprising a doubled-over or looped tubular mesh 232 and a cover 234. The cover 234 comprises a single layer mesh tube 231 that is heat shaped as described herein. The cover 234 comprises a proximal end 236 (bonded within a marker band 238) and a flared distal end 240 that is allowed to expand freely. The tubular mesh 232 comprises a first end 242 and a second end 244 that are also bonded within the marker band 238, and an intermediate portion 246 having a smooth apex 248. An inner surface 250 of a first leg 251 of the tubular mesh 232 may be configured to touch an inner surface 252 of a second leg 253 of the tubular mesh 232 when the tubular mesh 232 is in its expanded configuration. In other embodiments, the tubular mesh may be sized and configured such that the inner surfaces 250, 252 do not typically touch each other with the tubular mesh is in its expanded configuration. A proximal face 254 of the cover 234 is configured to be disposed against the proximal portion of an aneurysm, adjacent the neck of the aneurysm, to substantially provide occlusion of the neck. A maximum diameter portion 256 of the cover 234 may be configured to engage with a wall surface on the aneurysm. Additionally, a maximum transverse dimension portion 258 of the intermediate portion 246 of the mesh tube 232 is configured to engage a wall of the aneurysm.

Figure 18:
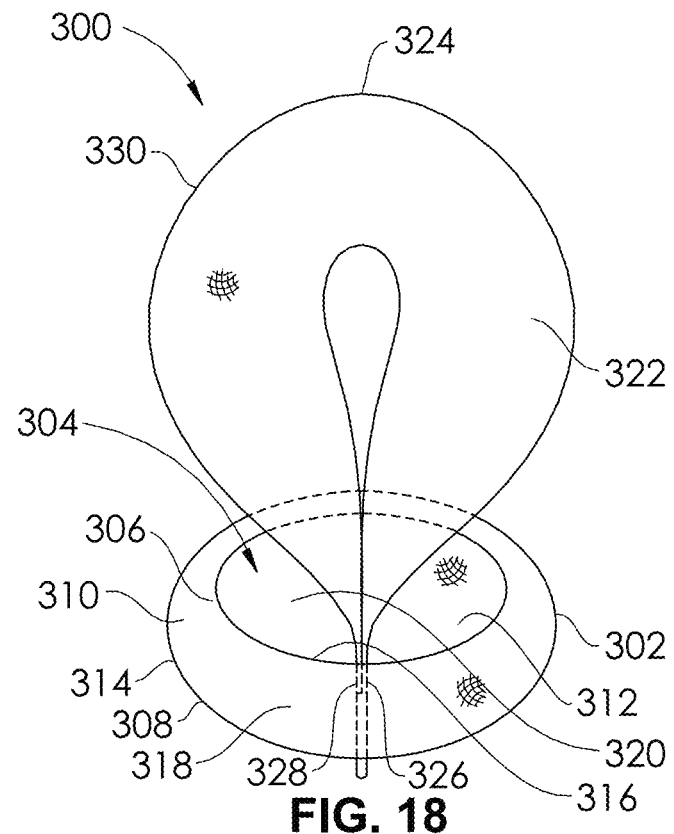
FIG. 18 is a perspective view of an occlusion device according to an alternative embodiment of the present disclosure.

FIG. 18 illustrates an occlusion device 300 comprising a cover 302 including a concavity 304 facing toward the distal end 306 of cover 302 and away from the proximal end 308 of the cover 302. The cover 302 is fabricated as an inverted mesh tube 310 having a simple straight elongate configuration, and is subsequently formed into the shape shown in FIG. 18, and heat set into this shape, as described previously herein. A smooth fold 316 extends around the distal end 306 cover 302 and represents the transition between an outer facing surface 318 and an inner facing surface 320. The occlusion device 300 is similar to the occlusion device 100 of FIG. 1, however an orifice 312 opening into the concavity 304 is smaller than the maximum diameter 314 of the cover 302. The orifice 312 has a diameter between about 35% and about 85% of the maximum diameter 314, or between about 45% and about 75%, or between about 50% and about 70%, or between about 55% and about 65%. Extending from the concavity 304 is a doubled-over or looped tubular mesh 322 having a smooth apex 324 configured to safely contact an interior wall of an aneurysm. The tubular mesh 322 has a first end 326 and a second end 328, and an intermediate portion 330 extending between the first end 326 and second end 328. The cover 302 and the tubular mesh 322 may have differing characteristics from each other in order to optimize the performance characteristics of each. In certain embodiments, the cover 302 may comprise between 36 and 144 filaments, each having a diameter between about 0.00075 to 0.001 inch. In a particular embodiment, the cover 302 may comprise 72 nickel-titanium filaments, each having a diameter of 0.00085 inch.

In certain embodiments, the tubular mesh 322 may comprise between 18 and 36 filaments, each having a diameter between about 0.00075 and 0.00125 inch. In the particular embodiment described in relation to the cover 302, the tubular mesh is constructed from 24 nickel titanium filaments, each having a diameter of 0.00093 inch. The particular diameters of 0.00085 and 0.00093 inch can be achieved by making the filaments with this diameter, or may be achieved by etching filaments having a slightly larger diameter (e.g., 0.001 inch) until the desired diameters are reached. In the particular embodiment, the cover 302 has a maximum diameter 314 (in the expanded state) of between about 4 mm and about 8 mm, or between about 5 mm and about 7 mm, or about 6 mm. The tubular mesh 322 has a diameter (in the expanded state) of between about 2 mm and 3 mm, or about 2.5 mm. In some embodiments some or all of the filaments may comprise drawn filled tubes (DFT) having a radiopaque cross-sectional fill area ratio of between about 10% to about 70%, or between about 51% to about 70%. The fill material can be platinum, or gold, or tantalum, or an alloy of any of these. The particular embodiment described has excellent compression in to a small diameter for delivery through a small catheter lumen, and has safe characteristics when expanded and delivered into an aneurysm.

Figure 19:
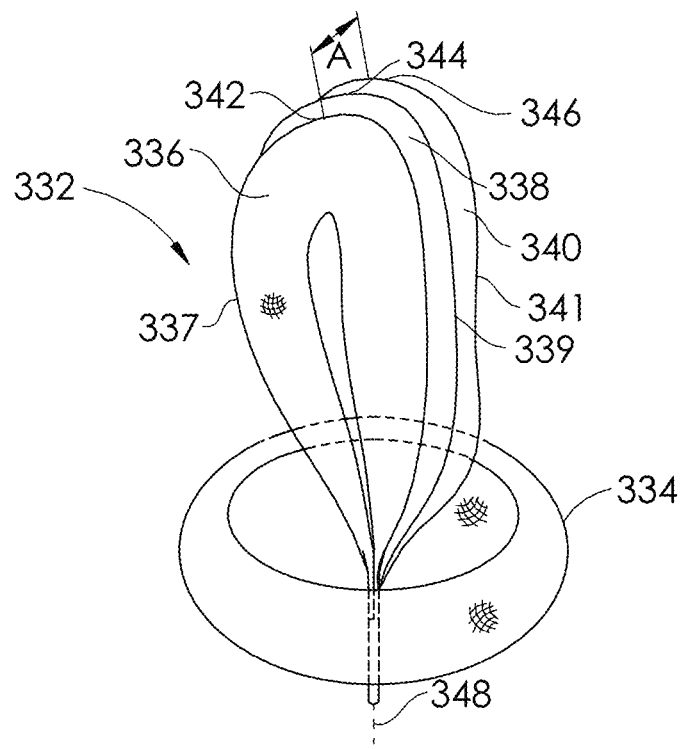
FIG. 19 is a perspective view of an occlusion device according to an alternative embodiment of the present disclosure.

FIG. 19 illustrates an occlusion device 332 comprising a cover 334 similar to the cover 302 of the occlusion device 300 of FIG. 18. However, there are three doubled-over or looped tubular meshes 336, 338, 340, each having a smooth apex 342, 344, 346, respectively. The three doubled-over or looped tubular meshes 336, 338, 340 are arrayed next to each other like books on a bookshelf. Because the diameter of their intermediate portions 337, 339, 341, in the expanded configuration, are greater than the diameter of their ends, the three doubled-over or looped tubular meshes 336, 338, 340 are fanned out. In some embodiments, the three doubled-over or looped tubular meshes 336, 338, 340 together form a fanned angle A that is between about 15° and about 90°, or between about 20° and about 75°, or between about 30° and about 60°. In alternative embodiments, the three doubled-over or looped tubular meshes 336, 338, 340 inhabit three substantially parallel planes that are not coplanar to each other, and are thus the three doubled-over or looped tubular meshes 336, 338, 340 are linearly arrayed in a transverse dimension to the longitudinal axis 348 of the cover 334.

Figure 20:
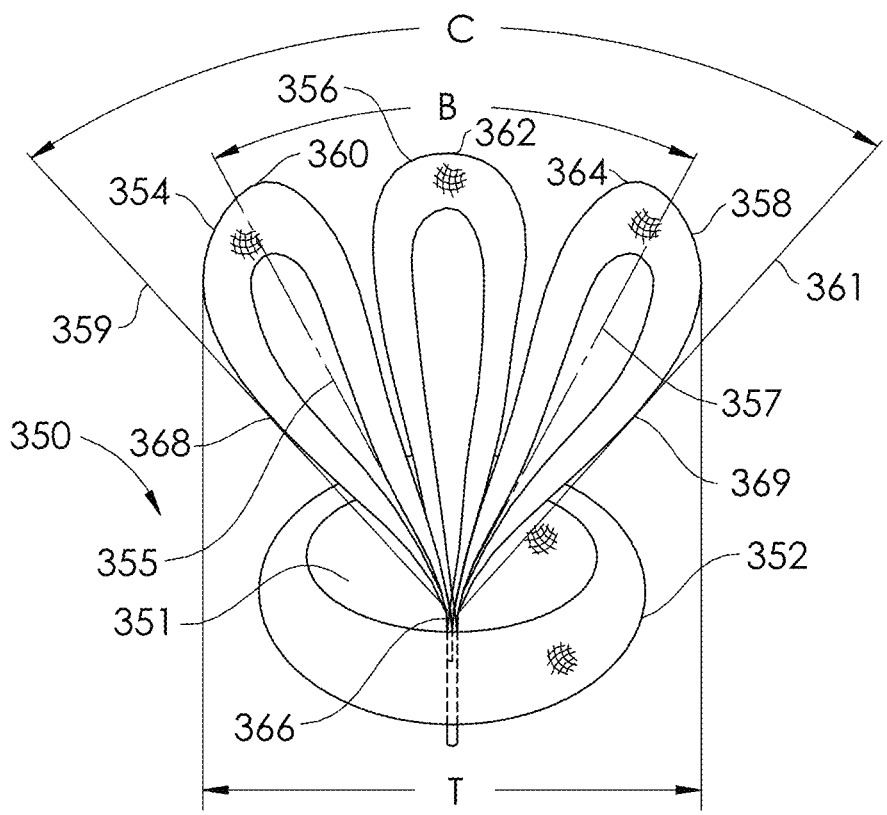
FIG. 20 is a perspective view of an occlusion device according to an alternative embodiment of the present disclosure.
Figure 21:
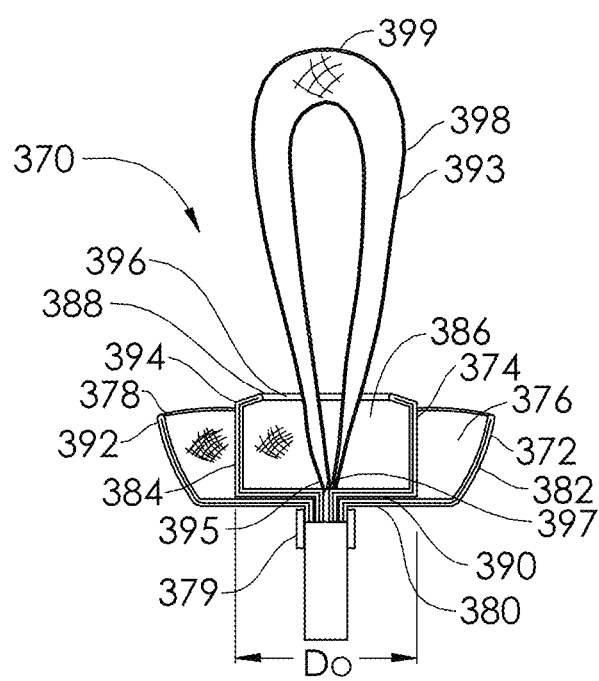
FIG. 21 is a longitudinal sectional view of an occlusion device according to an alternative embodiment of the present disclosure.

FIG. 20 illustrates an occlusion device 350 comprising a cover 352 having a concavity 351, the cover 352 similar to the cover 302 of the occlusion device 300 of FIG. 18. However, there are three doubled-over or looped tubular meshes 354, 356, 358, each having a smooth apex 360, 362, 364, respectively. The three doubled-over or looped tubular meshes 354, 356, 358 are arrayed next to each other like ribs of an opened folding hand fan. In some embodiments, all three of the looped tubular meshes 354, 356, 358 together approximate a single plane. In other embodiments, the looped tubular meshes 354, 356, 358 each approximate a different plane, together approximating an open triptych. In some embodiments, looped tubular meshes 354, 356, 358 together form a fanned angle B, between the centerline 355 of the first outside tubular mesh 354 and the centerline 357 of the second outside tubular mesh 358, that is between about 15° and about 120°, or between about 20° and about 90°, or between about 25° and about 75°, or between about 30° and about 60°. In some embodiments, looped tubular meshes 354, 356, 358 together form a fanned angle C, between the general outer contour line 359 of the first outside tubular mesh 354 and the general outer contour line 361 of the second outside tubular mesh 358, that is between about 20° and about 150°, or between about 30° and about 120°, or between about 30° and about 90°. The outer contour lines 359, 361 extend between the attachment 366 of the first and second ends of the tubular mesh and a maximal lateral extension point 368, 369. a maximum transverse dimension T is formed by the three looped tubular meshes 354, 356, 358, and is configured to contact the inner surface of an aneurysm at both sides, to stabilize the occlusion device 350 within the aneurysm. The cover 352 is configured to seal or occlude the aneurysm adjacent the neck, as in the other covers presented herein. FIG. 21 illustrates an occlusion device 370 comprising an outer cover 372 and an inner cover 374. The outer cover 372 includes a concavity 376 facing toward the distal end 378 of outer cover 372 and away from the proximal end 380 of the outer cover 372. The inner cover 374 is disposed within the concavity 376 of the outer cover 372 and includes a concavity 386 facing toward the distal end 388 of inner cover 374 and away from the proximal end 390 of the outer cover 374. The outer cover 372 has a distal flare 392, and the inner cover 374 has a maximum diameter 394 and a reduced diameter distal orifice 396. The covers 372, 374 are each fabricated as inverted mesh tubes 382, 384 having a simple straight elongate configuration, and subsequently formed into the shapes shown in FIG. 21, and heat set into these shapes, as described previously herein. Either of the covers 372, 374 may have the material or dimensional characteristic of any other of the covers described herein. An overlap dimension $D_O$ has an increased braid density, because it is substantially the braid densities (e.g., picks per inch) of the two covers 372, 374 combined. Thus, substantial stagnation of blood flow can be achieved at the neck of the aneurysm to thrombose and occlude the aneurysm. Extending from the concavity 386 is a doubled-over or looped tubular mesh 398 having a smooth apex 399 configured to safely contact an interior wall of an aneurysm. The tubular mesh 398 has a first end 397 and a second end 395, and an intermediate portion 393 extending between the first end 397 and second end 395. The outer cover 372, the inner cover 374, and the tubular mesh 398 may each have differing characteristics from each other in order to optimize the performance characteristics of each. In one embodiment, the inner cover 374 has a first braid density and the outer cover 372 has a second braid density that is greater than the first braid density. The tubular mesh 398 has a third braid density that is less than the first braid density. In some embodiments, the second braid density is between 110% and 200% of the first braid density. In some embodiments, the first braid density is between 110% and 200% of the third braid density. In certain embodiments, the outer cover 372 may comprise between 24 and 48 filaments, the inner cover 374 may comprise between 12 and 36 filaments, and the tubular mesh 398 may comprise between 6 and 24 filaments. Each filament may have a diameter between about 0.0006 to about 0.0015 inch, or between about 0.00075 to about 0.00125 inch. In a particular embodiment, the outer cover 372 may comprise 36 filaments, the inner cover 374 may comprise 24 filaments, and the tubular mesh 398 may comprise 12 filaments. The filaments may comprise nickel-titanium alloy, or DFT wires, or a combination thereof. The inner cover 374 additionally can serve to stabilize the tubular mesh 398, such that its loop remains substantially upright. The outer cover 372, at its distal flare 392 is configured to grip the inner wall of an aneurysm. As in all of the occlusion devices, a marker band 379 may be carried at an end of the occlusion device 370 and be configured to hold the ends 395, 397 and to be a radiopaque indicator of the proximal end of the occlusion device 370 on x-ray or fluoroscopy.

While the foregoing is directed to embodiments of the present disclosure, other and further embodiments may be devised without departing from the basic scope thereof. The filament diameter of the filaments comprising any of the mesh material (e.g., mesh tube including inverted mesh tubes) described herein may be between about 0.0004 inch and about 0.003 inch, or between about 0.0005 inch and about 0.002 inch, or between about 0.0006 inch and about 0.002 inch, or between about 0.0006 inch and about 0.0015 inch. The drawn filled tubes (DFT) may comprise between 0% and 100% of the total strands/filaments in any of the braided/mesh tubes. In some embodiments, the drawn filled tubes (DFT) comprise about 50% to about 100% of the total filaments of the cover and about 50% to about 100% of the total filaments of each of the doubled-over or looped tubular mesh. The radiopaque core of each of at least some of the drawn filled tubes has a cross-sectional area that is between about 10% and about 70% of the total cross-sectional area of the each of at least some of the drawn filled tubes, or between about 51% and about 70% of the total cross-sectional area of the each of at least some of the drawn filled tubes. In some embodiments, NiTi #1-DFT® wire produced by Fort Wayne Metals Research Products Corp. (Fort Wayne, IN USA) may be utilized. The filaments may be braided with patterns having filament crossings that are in any one or more of the following ratios of filaments: 1×1, 1×2, 2×1, 2×2, 2×3, 3×2, 3×3, etc. (e.g., warp and weft). Any low, moderate, or high pick counts may be used, for example, between about 15 picks per inch and about 300 picks per inch, or between about 20 picks per inch and about 160 picks per inch. Any of the filaments or any of the portion of the occlusion devices may be coated with compounds that enhance endothelialization, thus improving the healing process when implanted within the aneurysm, and optimizing occlusion. The pusher and occlusion device configurations presented herein may also be used for in other types of implantable devices, such as stents, flow diversion devices, filters, and occlusion devices for structural heart defects.

In some embodiments, braided elements may be subsequently etched (chemical etch, photochemical etch) to decrease the overall wire diameter and decrease the stiffness.

In any of the embodiments presented herein, the doubled-over or looped tubular mesh may be configured to engage a portion of the interior wall of the aneurysm, up to an including the majority of the wall of the entire aneurysm sac. In any of the embodiments presented herein that include a cover, the cover may be configured to engage with an interior wall of the aneurysm at or adjacent the neck of the aneurysm. The engagement may include a radial force. In some embodiments, the cover may be configured to cover the neck of the aneurysm without significantly engaging the aneurysm wall with a radial force.

Figure 22:
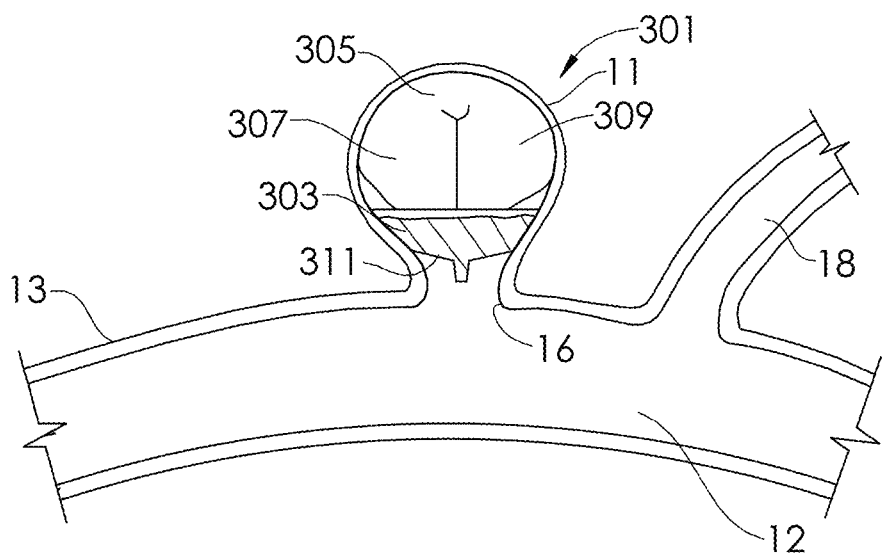
FIG. 22 is a view of an occlusion device implanted within an aneurysm according to an embodiment of the present disclosure.

Additional materials may be carried on a proximal portion of the cover, or any part of the occlusion device that is adjacent the neck of the aneurysm, in order to facilitate healing of the neck of the aneurysm. FIG. 22 illustrates an occlusion device 301 comprising a cover 303 that is coupled to a doubled-over or looped tubular mesh 305 having a first leg 307 and a second leg 309. The cover 303 includes a biological layer 311 configured to encourage growth. In some embodiments, the biological layer 311 may comprise antibodies, in order to accelerate the formation of an endothelial layer, for example, by attracting endothelial progenitor cells (EPCs). In some embodiments, the biological layer 311 may comprise a natural membrane or structure, such as a membrane, such as a membrane from an ear, or a cornea, or an ultra-thin piece of ligament, or even a piece of blood vessel wall.

Figure 23:
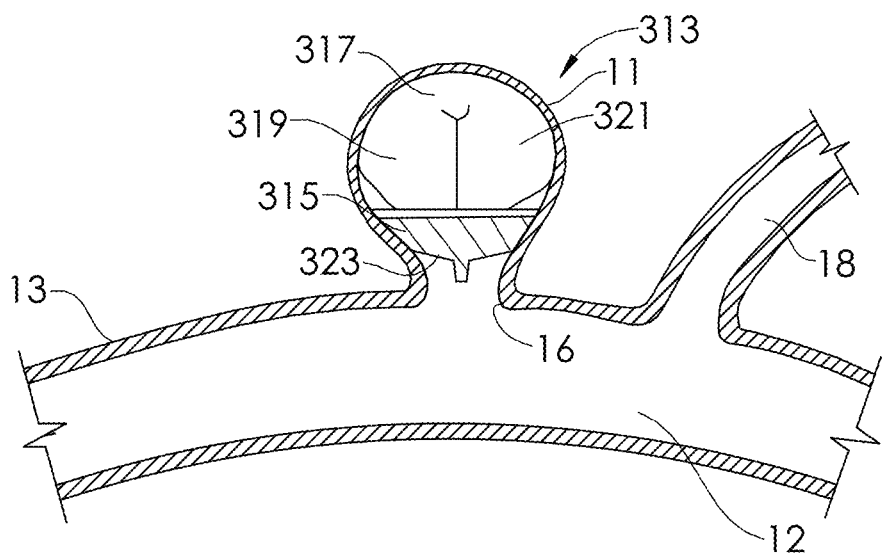
FIG. 23 is a view of an occlusion device implanted within an aneurysm according to an embodiment of the present disclosure.

FIG. 23 illustrates an occlusion device 313 comprising a cover 315 that is coupled to a doubled-over or looped tubular mesh 317 having a first leg 319 and a second leg 321. The cover 315 includes a polymer layer 323 configured to act as a simulated arterial wall. In some embodiments, the polymer layer 323 may comprise polytetrafluoroethylene, such as expanded polytetrafluoroethylene (ePTFE), such as that used in grafts.

The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

For purposes of the present disclosure and appended claims, the conjunction "or" is to be construed inclusively (e.g., "an apple or an orange" would be interpreted as "an apple, or an orange, or both"; e.g., "an apple, an orange, or an avocado" would be interpreted as "an apple, or an orange, or an avocado, or any two, or all three"), unless: (i) it is explicitly stated otherwise, e.g., by use of "either . . . or," "only one of," or similar language; or (ii) two or more of the listed alternatives are mutually exclusive within the particular context, in which case "or" would encompass only those combinations involving non-mutually-exclusive alternatives. For purposes of the present disclosure and appended claims, the words "comprising," "including," "having," and variants thereof, wherever they appear, shall be construed as open-ended terminology, with the same meaning as if the phrase "at least" were appended after each instance thereof.

What is claimed is:

1. A method for treating an aneurysm, comprising:
providing an occlusion device releasably coupled to an elongate delivery shaft and comprising a cover and a looped mesh tube, the cover comprising a braided tube inverted into a two-layer structure, and the braided tube having first and second ends at a proximal end of the cover, the two-layer structure comprising a distal concavity, the looped mesh tube having first and second ends held within the cover;

advancing a distal end of a delivery catheter having a delivery lumen to a location adjacent the aneurysm;

advancing the occlusion device through the delivery lumen of the delivery catheter, with the cover and the looped mesh tube each compressed into a compressed state;

advancing the occlusion device out of the delivery lumen of the delivery catheter at the distal end of the delivery catheter, and into the aneurysm, such that the cover and the looped mesh tube each expand: and detaching the occlusion device from the elongate delivery shaft.

2. The method of claim 1, wherein the aneurysm is a previously ruptured aneurysm.

3. The method of claim 1, wherein the looped mesh tube comprises a first leg, a second leg, and an apex of a curve connecting the first leg and the second leg.

4. The method of claim 3, wherein advancing the occlusion device out of the delivery lumen comprises advancing the occlusion device such that the apex of the curve begins to exit the delivery lumen first.

5. The method of claim 3, wherein the looped mesh tube is delivered such that the apex of the curve contacts an aneurysm wall.

6. The method of claim 1, wherein the cover is expanded against an aneurysm wall at or adjacent a neck portion of the aneurysm.

7. The method of claim 6, wherein the looped mesh tube comprises a first leg, a second leg, and an apex of a curve connecting the first leg and the second leg and wherein the apex of the curve contacts the aneurysm wall.

8. The method of claim 1, wherein the first and second ends of the looped mesh tube are secured next to each other within the cover.

9. The method of claim 1, wherein the first end of the looped mesh tube comprises a cut in a wall the looped mesh tube and wherein the second end, in a collapsed configuration, is held within the first end of the looped mesh tube.

10. The method of claim 1, wherein the cover in a fully expanded state has a cover diameter and wherein the looped mesh tube in an expanded state has a maximum transverse dimension, the maximum transverse dimension greater than the cover diameter.

11. The method of claim 1, wherein the cover is circular.

12. The method of claim 1, wherein the cover comprises nickel-titanium alloy.

13. The method of claim 1, wherein the occlusion device comprises a radiopaque material.

14. The method of claim 1, further comprising:
inserting the delivery catheter through a sheath.

15. The method of claim 14, wherein the sheath has been placed through puncture in a radial artery.

16. The method of claim 1, wherein the aneurysm comprises a cerebral aneurysm.

17. The method of claim 1, wherein the looped mesh tube in an expanded state comprises a first leg, a second leg, and an intermediate portion between the first leg and the second leg.

18. The method of claim 17, wherein the first leg is configured to substantially contact the second leg at a central axis.

19. The method of claim 17, wherein the first leg and the second leg together form a first transverse dimension and a second transverse dimension, wherein the first transverse dimension is greater than the second transverse dimension.

20. The method of claim 1, wherein detaching the occlusion device comprises utilizing an energy comprising one of: hydraulic, electrolytic, mechanical, thermal, and chemical.

* * * * *